US012590164B2

(12) United States Patent
Kim et al.

(10) Patent No.: US 12,590,164 B2
(45) Date of Patent: Mar. 31, 2026

(54) PRODUCTIVITY-ENHANCED ANTIBODY AND METHOD FOR PRODUCING SAME

(71) Applicant: Yonsei University BioHealth Technology Holdings, Inc., Seoul (KR)

(72) Inventors: Joo Young Kim, Gyeonggi-do (KR); Jinu Lee, Incheon (KR); Hye Yeon Kim, Seoul (KR)

(73) Assignee: Yonsei University BioHealth Technology Holdings, Inc., Seoul (KR)

( * ) Notice: Subject to any disclaimer, the term of this patent is extended or adjusted under 35 U.S.C. 154(b) by 1386 days.

(21) Appl. No.: 17/285,836

(22) PCT Filed: Oct. 4, 2019

(86) PCT No.: PCT/KR2019/013008
§ 371 (c)(1),
(2) Date: Apr. 15, 2021

(87) PCT Pub. No.: WO2020/080715
PCT Pub. Date: Apr. 23, 2020

(65) Prior Publication Data
US 2021/0388101 A1    Dec. 16, 2021

(30) Foreign Application Priority Data
Oct. 15, 2018    (KR) ........................ 10-2018-0122775

(51) Int. Cl.
*C07K 16/28*    (2006.01)
(52) U.S. Cl.
CPC ...... *C07K 16/2887* (2013.01); *C07K 16/2818* (2013.01); *C07K 2317/14* (2013.01); *C07K 2317/24* (2013.01); *C07K 2317/41* (2013.01)
(58) Field of Classification Search
None
See application file for complete search history.

(56) References Cited

U.S. PATENT DOCUMENTS

| | | |
|---|---|---|
| 5,736,137 A | 4/1998 | Anderson et al. |
| 5,776,456 A | 7/1998 | Anderson et al. |
| 8,008,449 B2 | 8/2011 | Korman et al. |
| 8,686,119 B2 | 4/2014 | Rotem-Yehudar et al. |

FOREIGN PATENT DOCUMENTS

| | | |
|---|---|---|
| EP | 2000149 | 5/2009 |
| WO | 2004035607 | 4/2004 |
| WO | 2004056312 | 7/2004 |
| WO | 2005103081 | 11/2005 |
| WO | 2006121168 | 11/2006 |
| WO | 2009101611 | 8/2009 |
| WO | 2010128145 A1 | 11/2010 |
| WO | 2013014558 | 1/2013 |
| WO | 2015135884 | 9/2015 |
| WO | 2018136891 A1 | 7/2018 |

OTHER PUBLICATIONS

Haryadi et al (PLOS, 10(2):e0116878, pp. 1-16).*
Kim et al (BBE, 43:863-875, 2020).*
International Search Report and Written Opinion mailed Feb. 5, 2020 in International Patent Application No. PCT/KR2019/013008.
Martinez, "Characterization of a novel modification on IgG2 light chain: Evidence for the presence of O-linked mannosylation", Journal of Chromatography A, 2007.
Hastings, "Inhibition of 0-G1cNAcase leads to elevation of 0-G1cNAc tau and reduction of tauopathy and cerebrospinal fluid tau in rTg4510 mice", Molecular neurodegeneration, 2017.
Valliere-Douglass, "0-fucosylation of an antibody light chain: characterization of a modification occuring on an IgG1 molecule", Glycobiology, 2009.
Martinez et al., "Characterization of a novel modification on IgG2 light chain Evidence for the presence of O-linked mannosylation", Journal of Chromatography, 2007.
Hastings et al., "Inhibition of O-GlcNAcase leads to elevation of O-GlcNAc tau and reduction of tauopathy and cerebrospinal fluid tau in rTg4510 mice", Research Article, BioMed Central, 2017.
Valliere-Douglass et al., "O-Fucosylation of an antibody light chain: Characterization of a modification occurring on an IgG1 molecule", Glycobiology vol. 19 No. 2 pp. 144-152, 2009.
Kim, "Improvement the rituximab production by O-GlcNAcylation using Thiamet G", Yonsei University, 2019.
Anderson et al., "Expression of Human B Cell-Associated Antigens on Leukemias and Lymphomas: A Model of Human B Cell Differentiation", Blood, vol. 63, No. 6, 1984.
Armand, P. et al., "Disabling Immune Tolerance by Programmed Death-1 Blockade with Pidilizumab after autologous hematopoietic stem-cell transpantation for diffuse large b-cell lymphoma: results of an international phase II trial", J Clin Oncol 31, 4199-4206 (2013).
Berger, R. et al., "Phase I Safety and Pharmacokinetic Study of CT-011, a Humanized Antibody Interacting with PD-1, in Patients with Advanced Hematologic Malignancies", Clinical Cancer Research 14, 3044-3051 (2008).
Einfeld et al., "Molecular cloning of the human B cell CD20 receptor predicts a hydrophobic protein with multiple transmembrane domains", EMBO J. 7 (3) 711-717 (1988).
Gobom et al., "Sample Purification and Preparation Technique Based on Nano-scale Reversed-phase Columns for the Sensitive Analysis of Complex Peptide Mixtures by Matrix-assisted Laser Desorption/Ionization Mass Spectrometry", Journal of Mass Spectrometry, 1999.
Hamid, O. et al., "Safety and Tumor Responses with Lambrolizumab (Anti-PD-1) in Melanoma", N Engl J Med 369, 134-144 (2013).
(Continued)

*Primary Examiner* — Brad Duffy
(74) *Attorney, Agent, or Firm* — Polsinelli PC

(57)    ABSTRACT

Provided herein is a method for producing an antibody with improved productivity while maintaining its titer by causing at least one hydroxyamino acid contained in the light chain of the antibody to undergo O-linked glycosylation. Also provided is an antibody so produced.

4 Claims, 24 Drawing Sheets

Specification includes a Sequence Listing.

(56) References Cited

OTHER PUBLICATIONS

Reff at al, "Depletion of B Cells In Vivo by a Chimeric Mouse Human Monoclonal Antibody to CD20", Blood 83 (2) 435-445 (1994).

Tedder et al., "The B cell surface molecule B1 is functionally linked with B cell activation and differentiation", J. Immunol. 135 (2) 973-979 (1985).

Topalian, S.L. et al., "Targeting the PD-1/B7-H1 (PD-L1) pathway to activate anti-tumor immunity", Current Opinion in Immunology 24, 207-212 (2012).

Topalian, S.L. et al., "Safety, Activity, and Immune Correlates of Anti-PD-1 Antibody in Cancer", N Engl J Med 366, 2443-2454 (2012).

Valentine et al., "Phosphorylation of the CD20 Phosphoprotein in Resting B Lymphocytes", J. Biol. Chem. 264 (19) 11282-11287 (1989).

Wang et al., "In Vitro Characterization of the Anti-PD-1 Antibody Nivolumab, BMS-936558, and In Vivo Toxicology in Non-Human Primates", Cancer Immunol Res. 2, 846-56 (2014).

Topalian, et al., "Survival Durable Tumor Remission, and Long-Term Safety in Patients with Advanced Melanima Receiving Nivolumab", Journal of Clinical Oncology 32, No. 10 (Apr. 1, 2014) 1020-1030.

Wang et al., "dbOGAP—An Integrated Bioinformatics Resource for Protein O-GlcNAcylation", BMC Bioinformatics 2011, 12, 91.

Chandrasekaran, E.V. et al. (1981) "Structures of Sialylated O-Glycosidically and N-Glycosidically Linked Oligosaccharides in a Monoclonal Immunoglobulin Light Chain" JBC 256:4 pp. 1549-1555.

Krishnan, I.S., et al. (1999) "Co-Secretion of Two Distinct Kappa Light Chains by the Mu-9 Hybridoma" Hybridoma. 18:4, pp. 325-333.

Cragg, M.S., et al. (2004) "Antibody specificity controls in vivo effector mechanisms of anti-CD20 reagents" Blood. 103:7 pp. 2738-2743.

Cragg, M.S. et al. (2003) "Complement-mediated lysis by anti-CD20 mAb correlates with segregation into lipid rafts" Blood. 101:3 pp. 1045-1052.

Topalian, S.L., et al. (2013) "Nivolumab (anti-PD-1; BMS-936558; ONO-4538) in patients with advanced solid tumors: Survival and long-term safety in a phase I trial" J Clin Oncol. 31:15 Suppl p. 3002.

* cited by examiner (a)

(b)

IB : O-GlcNAc
(RL2-HRP)

(a)

IB : human+mouse IgG (b)

| | Num. | S/T | Percentage %(Matching A.A) | |
|---|---|---|---|---|
| NT | 208 | S | 5 | (1/21) |
| TMG | 7 | S | 100 | (1/1) |
| | 12 | S | 100 | (1/1) |
| | 14 | S | 100 | (1/1) |
| | 181 | S | 33 | (1/3) |

FIG. 10

RTX_LC (SEQ ID NO:19)

FIG. 11

<Non-Reducing>

| Num. | S/T | Percentage%(Matching A.A) | |
| --- | --- | --- | --- |
| | | NT | TMG |
| 42 | S | 9.1 (3/33) | 18.2 (4/22) |
| 51 | S | 11.8 (2/17) | 5.9 (2/34) |
| 55 | S | 41.2 (7/17) | 5.9 (2/34) |
| 91 | T | 4.3 (1/23) | 5.3 (1/19) |
| 101 | T | 30.4 (7/23) | 15.8 (3/19) |
| 155 | S | 7.7 (5/65) | 4.4 (3/68) |
| 181 | S | 6.2 (4/65) | 5.3 (3/57) |

FIG. 18

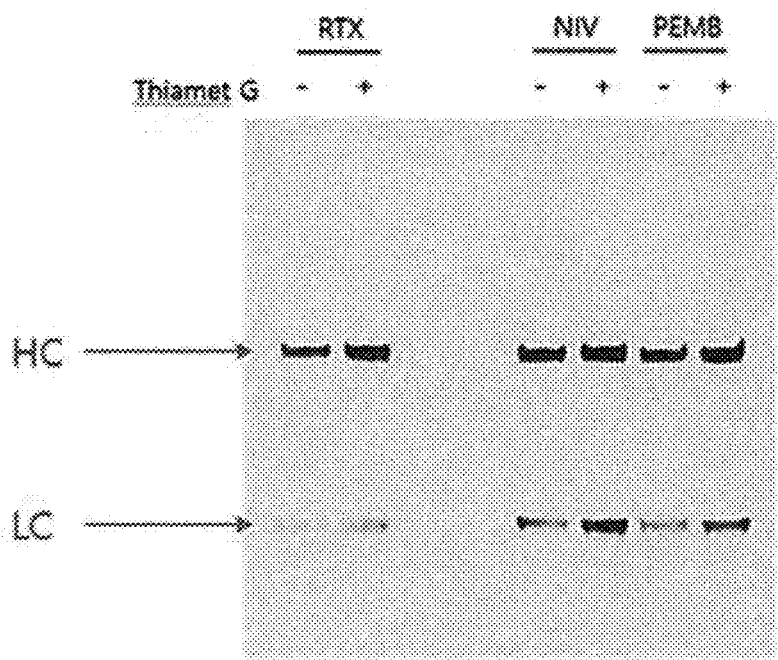
FIG. 19
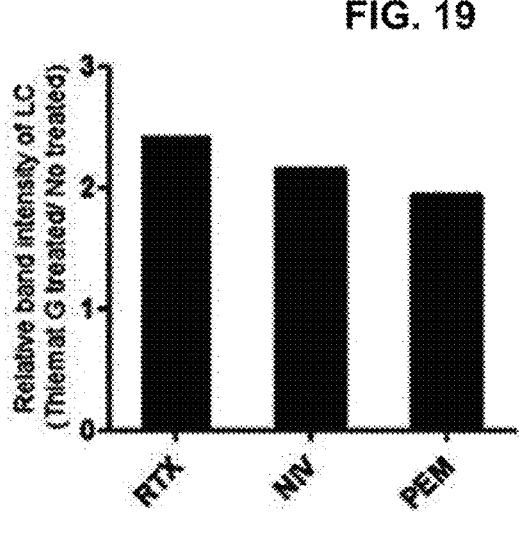
FIG. 20
NIV_LC        EIYLTQSPATLSLSPGERATLSCRASQSVSS-------YLAWYQQKPGQAPRLLIYDASNRA (SEQ ID NO: 20)
Pemb_LC       EIYLTQSPATLSLSPGERATLSCRASKGYSTSG-YSYLHWYQQKPGQAPRLLIYLASYLE (SEQ ID NO: 21)
RTX_LC        QIYLSQSPAILSASPGEKVTMTCRASSSVSY-------IHWFQQKPGSSPKPWIYATSNLA (SEQ ID NO: 22)
FIG. 21

H+M(1:1)

H+M(1:2)

H+M(1:1)
high expose WB

1

PRODUCTIVITY-ENHANCED ANTIBODY AND METHOD FOR PRODUCING SAME

CROSS-REFERENCE TO RELATED APPLICATIONS

This application is U.S. national phase application under 35 U.S.C. § 371 of International Application No. PCT/KR2019/013008, filed on Oct. 4, 2019, which claims the benefit of priority to Korean Patent Application No. KR10-2018-0122775, filed on Oct. 15, 2018, the contents of each of which are incorporated herein by reference in their entirety.

STATEMENT REGARDING SEQUENCE LISTING

The instant application contains a Sequence Listing which has been submitted via ASCII copy created on Oct. 15, 2018, named "21-2011-WO-US_Seq_Listing_ST25.txt" having 22 sequences.

FIELD

The present disclosure generally relates to antibodies. More specifically, the present disclosure relates to antibodies with improved productivity and methods for producing the same.

BACKGROUND

CD20 antigen (also called human B-lymphocyte-restricted differentiation antigen, Bp35) is a hydrophobic transmembrane protein which has a molecular weight of approximately 35 kD and is located on pre-B and mature B lymphocytes (Valentine et al., J. Biol. Chem. 264 (19): 11282-11287 (1989); and Einfeld et al., EMBO J. 7 (3): 711-717 (1988)). The antigen is also expressed on >90% of B-cell non-Hodgkin's lymphomas (Anderson et al., Blood 63 (6): 1424-1433 (1984)), but is not found on hematopoietic stem cells, pro-B cells, normal plasma cells, or other normal tissues (Tedder et al., J. Immunol. 135 (2): 973-979 (1985)). CD20 regulates (an) early step(s) in the activation process for cell cycle initiation and differentiation (Tedder et al., supra), and possibly functions as a calcium ion channel (Tedder et al. J. Cell. Biochem. 14D: 195 (1990)).

B-cell lymphomas express CD20. Thus this antigen has been a useful therapeutic target for treating such lymphomas. There are more than 300,000 people afflicted with B-cell NHL in the United States, and more than 56,000 new cases are diagnosed each year. Rituximab (RITUXAN®) antibody (available from Genentech, Inc., South San Francisco, California, USA), which is a genetically engineered chimeric murine/human monoclonal antibody directed against human CD20 antigen, is used for treatment of patients suffering from relapsed or refractory low grade or follicular CD20 positive, B cell non-Hodgkin's lymphoma. Rituximab is an antibody referred to as "C2B8" in U.S. Pat. No. 5,736,137 (Anderson et al.), issued Apr. 9, 1998, and U.S. Pat. No. 5,776,456. In vitro mechanism of action studies have demonstrated that RITUXAN® binds human complement and lyses lymphoid B-cell lines through complement-dependent cytotoxicity (CDC) (Reff et al., Blood 83 (2): 435-445 (1994)). Additionally, RITUXAN® has significant activity in assays for antibody-dependent cell-mediated cytotoxicity (ADCC). In vivo preclinical studies have shown that RITUXAN® depletes B cells from the peripheral blood, lymph nodes, and bone marrow of cynomolgus monkeys, presumably through complement- and cell-mediated processes (Reff et al., Blood 83 (2): 435-445 (1994)).

There is a need for antibodies with improved productivities and methods for producing the same. The present disclosure fulfills this need.

SUMMARY

The present disclosure provides, in part, an antibody with improved productivity while maintaining its titer to a level that is equivalent to or higher than the original antibody, and methods for producing or using the same.

Accordingly, one aspect of the present disclosure provides an antibody that comprises at least one glycosylated hydroxyamino acid residue in the light chain thereof. In one embodiment, the antibody provided herein comprises at least one glycosylated serine, glycosylated threonine, or glycosylated tyrosine in the light chain.

In one embodiment, the antibody comprises at least one glycosylated hydroxyamino acid residue at the $7^{th}$, $12^{th}$, $14^{th}$, $26^{th}$, $51^{st}$, $55^{th}$, $62^{nd}$, $101^{st}$, $155^{th}$, or $181^{st}$, position from the 5' end of the light chain.

In one embodiment, the antibody comprises at least one glycosylated hydroxyamino acid residue at the $7^{th}$, $12^{th}$, or $14^{th}$ position from the 5' end of the light chain.

In one embodiment, the glycosylation is O-linked glycosylation such that N-acetylglucosamine is bound to the at least one hydroxyamino acid residue in the light chain.

In one embodiment, the antibody disclosed herein is anti-CD20 antibody or an anti-PD-1 antibody. By way of non-limiting example, the anti-CD20 antibody is rituximab comprising at least one glycosylated hydroxyamino acid residue at the $7^{th}$, $12^{th}$, $14^{th}$, $26^{th}$, $51^{st}$, $55^{th}$, $62^{nd}$, $101^{st}$, $155^{th}$, or $181^{st}$ position from the 5' end of the light chain. Still by way of non-limiting example, the anti-PD-1 antibody is nivolumab, pembrolizumab, or pidilizumab comprising at least one glycosylated hydroxyamino acid residue at the $7^{th}$, $12^{th}$, or $14^{th}$ position from the 5' end of the light chain.

Another aspect of the present disclosure provides a method of producing an antibody by glycosylating at least one hydroxyamino acid residue in the light chain thereof.

In one embodiment, the at least one hydroxyamino acid residue is serine, threonine, or tyrosine in the light chain. In one embodiment, the at least one hydroxyamino acid residue is at the $7^{th}$, $12^{th}$, $14^{th}$, $26^{th}$, $51^{st}$, $55^{th}$, $62^{nd}$, $101^{st}$, $155^{th}$, or $181^{st}$ position from the 5' end of the light chain. In one embodiment, the at least one hydroxyamino acid residue is at the $7^{th}$, $12^{th}$, or $14^{th}$ position from the 5' end of the light chain.

In one embodiment, the method further comprises transforming a host cell with at least one recombinant nucleic acid molecule that encodes the antibody or light or heavy chain thereof, and culturing the transformed host cell to produce the antibody. In one embodiment, an O-GlcNAcase inhibitor is added during the culturing step.

By way of non-limiting example, the O-GlcNAcase inhibitor is selected from the group consisting of Thiamet-G, streptozotocin (STZ), PUGNAc, NAG-thiazoline, NButGT, (2R,3S)-iminocyclitol, PUGNAc-imidazole hybrid, and GlcNAcstatin C.

Yet another aspect of the present disclosure provides a method of preventing or treating a proliferative disease in a subject in need thereof. Such method comprises administering to the subject a therapeutically effective amount of the antibody disclosed above and herein. In one embodiment, the proliferative disease is a cancer.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 10 illustrates positions of serine residues, to which O-GlcNAc is bound and which are obtained through LC- MS/MS analysis, in the light chain of a rituximab antibody in a case where Thiamet-G is added.

FIG. 11 illustrates positions of serine residues, to which O-GlcNAc is predicted to be bound and which are obtained through an application-providing program (OGAP), in the light chain of a rituximab antibody in a case where Thiamet-G is added.

FIG. 18 illustrates changes in degree of binding of O-GalNAc, which are obtained through LC-MS/MS analysis, in the light chain of a rituximab antibody in a case where Thiamet G is added and a case where Thiamet G is not added.

FIG. 19 illustrates results obtained by analyzing, through Western blotting, changes in expression level of the heavy and light chains of each antibody after addition of Thiamet-G, when each of rituximab (RTX), nivolumab (NW), and pembrolizumab (PEMB) is expressed using host cells.

FIG. 20 graphically illustrates changes in expression level of the light chain of each antibody after addition of Thiamet-G, when each of rituximab (RTX), nivolumab (NIV), and pembrolizumab (PEMB) is expressed using host cells.

FIG. 21 illustrates results obtained by comparing the light chain sequences of rituximab (RTX), nivolumab (NIV), and pembrolizumab (PEMB).

DETAILED DESCRIPTION

Figure 1:
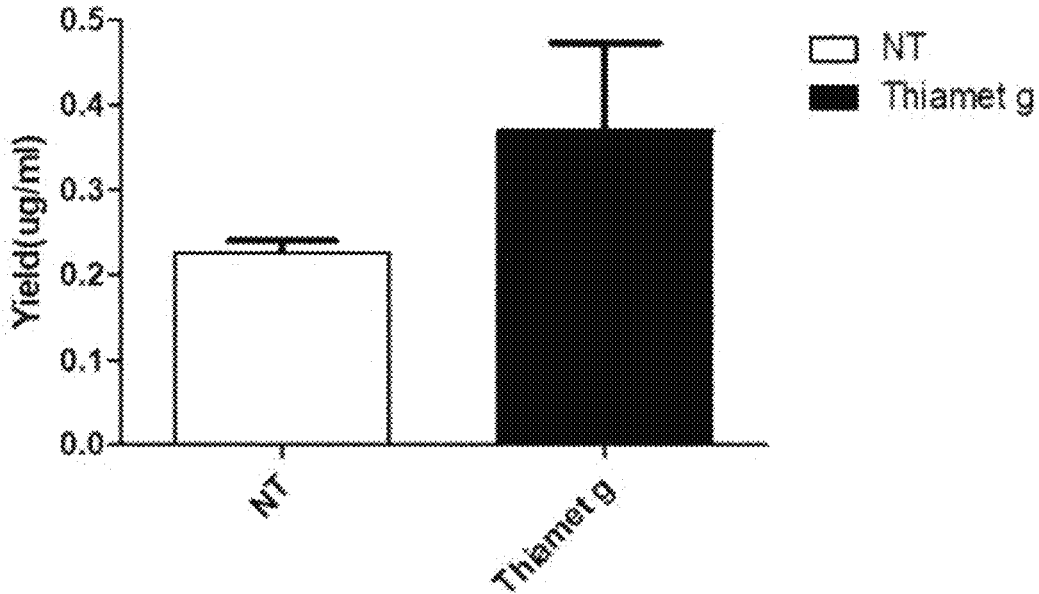
FIG. 1 graphically illustrates results obtained by comparing the production yield of a rituximab antibody, which is expressed in a case where Thiamet-G is added and a case where Thiamet-G is not added.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Section headings as used in this section and the entire disclosure herein are merely for organizational purposes and are not intended to be limiting.

An object of the present disclosure is to provide a method for improving productivity of various antibodies as well as to provide antibodies with improved productivity while maintaining their titers equivalent to or higher than the original antibodies. However, the technical problem to be solved by the present disclosure is not limited to the above-mentioned problems. Other problems which are not explicitly mentioned will be clearly understood by those skilled in the art from the following description.

The solution provided by the present disclosure is provision of glycosylated antibodies as well as methods of producing the same. Accordingly, one aspect of the present disclosure provides an antibody that comprises at least one glycosylated hydroxyamino acid residue in the light chain thereof. The antibody may be any antibody, without limitation, as long as the antibody contains at least one hydroxyamino acid residue in the light chain. By way of non-limiting example, the at least one hydroxyamino acid residue is in the light chain variable region.

A suitable antibody comprises at least one hydroxyamino acid residue to be glycosylated that has a hydroxyl group in the molecule. By way of non-limiting example, such hydroxyamino acid residue may be serine (Ser), threonine (Thr), or tyrosine (Tyr). By way of non-limiting example, the hydroxyamino acid residue may be a serine (Ser) or threonine (Thr) residue.

In one embodiment, the antibody may comprise at least one hydroxyamino acid residue at one of the $7^{th}$, $12^{th}$, $14^{th}$, $26^{th}$, $51^{st}$, $55^{th}$, $62^{nd}$, $101^{st}$, $155^{th}$, and $181^{st}$ positions from the 5' end of the light chain. By way of non-limiting example, the at least one hydroxyamino acid residue is in the light chain variable region. The amino acid position numbering may be according to EU index as in Kabat, but is not limited thereto.

In one embodiment, the antibody may comprise at least one hydroxyamino acid residue at one of the $7^{th}$, $12^{th}$, and $14^{th}$ positions from the 5' end of the light chain. By way of non-limiting example, the at least one hydroxyamino acid residue is in the light chain variable region.

By way of non-limiting example, the antibody may be an anti-CD20 antibody or an anti-PD-1 antibody.

An "anti-CD20 antibody" is an antibody that specifically binds to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al., Blood 103 (2004): 2738-2743; and Cragg, M. S., et al., Blood 101 (2003): 1045-1052.

By way of non-limiting example, the anti-CD20 antibody may be a type I anti-CD20 antibody, including but not limited to, rituximab, HI47 IgG3 (ECACC, hybridoma), 2C6 IgG1 (as disclosed in WO 2005/103081), 2F2 IgG1 (as disclosed in WO 2004/035607 and WO 2005/103081), or 2H7 IgG1 (as disclosed in WO 2004/056312). By way of non-limiting example, the anti-CD20 antibody may be a rituximab antibody.

A "rituximab" antibody is a genetically engineered chimeric human gamma 1 murine constant region-containing monoclonal antibody directed against human CD20 antigen. By way of non-limiting example, the chimeric antibody may include a human immunoglobulin G1 (IgG1) heavy chain constant region represented by SEQ ID NO: 1; a human kappa light chain constant region represented by SEQ ID NO: 2; a murine heavy chain variable region represented by SEQ ID NO: 3; and a murine light chain variable region represented by SEQ ID NO: 4. That is, by way of non-limiting example, the chimeric antibody may consist of two heavy chains represented by SEQ ID NO: 5 and two light chains represented by SEQ ID NO: 6. Rituximab is identified by the name "C2B8" in EP2000149B1 (Anderson et al.). Rituximab is approved for treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff et al., Blood 83(2): 435-445 (1994)). In addition, rituximab exhibits significant activity in assays that measure antibody-dependent cell-mediated cytotoxicity (ADCC).

By way of non-limiting example, wherein the anti-PD-1 antibody may be a nivolumab, pembrolizumab, or pidilizumab antibody. A "nivolumab" antibody (trade name OPDIVO®; formerly designated 5C4, BMS-936558, MDX-1106, or ONO-4538) is a fully humanized IgG4 (S228P) PD-1 antibody that selectively prevents interaction with PD-1 ligands (PD-L1 and PD-L2), thereby blocking the down-regulation of antitumor T-cell functions (U.S. Pat. No. 8,008,449; WO2006/121168; Wang et al., Cancer Immunol Res. 2: 846-56 (2014); Topalian, S. L. et al., N Engl J Med 366: 2443-2454 (2012); Topalian, S. L. et al., Current Opinion in Immunology 24:207-212 (2012); Topalian, S. L. et al., J Clin Oncol 31 (suppl): 3002 (2013)). By way of non-limiting example, the nivolumab antibody may include a heavy chain variable region represented by SEQ ID NO: 7 and a light chain variable region represented by SEQ ID NO: 8, or may consist of a heavy chain represented by SEQ ID NO: 9 and a light chain represented by SEQ ID NO: 10.

A "pembrolizumab" antibody (trade name KEYTRUDA®; also known as lambrolizumab and MK-3475) is a humanized monoclonal IgG4 kappa antibody directed against PD-1 which contains an S228P mutation (Hamid, O. et al., N Engl J Med 369:134-144 (2013)). The pembrolizumab antibody may include a heavy chain variable region represented by SEQ ID NO: 11 and a light chain variable region represented by SEQ ID NO: 12, or may consist of a heavy chain represented by SEQ ID NO: 13 and a light chain represented by SEQ ID NO: 14.

A "pidilizumab" antibody (also known as CT-011 and MDV9300) is a humanized IgG1 kappa monoclonal antibody that binds to PD-1. Pidilizumab is in development by Medivation for treatment of cancer and infectious diseases. Pidilizumab is described, e.g., in U.S. Pat. No. 8,686,119 B2, WO 2013/014668 A1, WO2009/101611, Berger, R. et al., Clinical Cancer Research 14: 3044-3051 (2008), and Armand, P. et al., J Clin Oncol 31: 4199-4206 (2013). By way of non-limiting example, the pidilizumab antibody may include a heavy chain variable region represented by SEQ ID NO: 15 and a light chain variable region represented by SEQ ID NO: 16, or may consist of a heavy chain represented by SEQ ID NO: 17 and a light chain represented by SEQ ID NO: 18.

The present disclosure provides a glycosylated antibody as a suitable solution, wherein at least one hydroxyamino acid residue contained in the light chain may be glycosylated. By way of non-limiting example, the at least one hydroxyamino acid residue is in the light chain variable region. By way of non-limiting example, the at least one hydroxyamino acid residue may be a serine (Ser), threonine (Thr), or tyrosine (Tyr) residue. By way of non-limiting example, at least one serine (Ser) or threonine (Thr) residue contained in the light chain variable region may be glycosylated. By way of non-limiting example, at least one serine (Ser) residue contained in the light chain variable region may be glycosylated.

In one embodiment, the glycosylation may occur to at least one hydroxyamino acid residue at the $7^{th}$, $12^{th}$, $14^{th}$, $26^{th}$, $51^{st}$, $55^{th}$, $62^{nd}$, $101^{st}$, $155^{th}$, or $181^{st}$ position from the 5' end of the light chain of the antibody. By way of non-limiting example, the glycosylation may occur to at least one hydroxyamino acid residue at the $7^{th}$, $12^{th}$, $14^{th}$, $26^{th}$, or $62^{nd}$ position from the 5' end of the light chain variable region of the antibody. Still by way of non-limiting example, the glycosylation may occur to at least one hydroxyamino acid residue at the $7^{th}$, $12^{th}$, or $14^{th}$ position from the 5' end of the light chain variable region of the antibody. The amino acid position numbering may be according to EU index as in Kabat, but is not limited thereto.

In one embodiment, the antibody is an anti-CD20 antibody or an anti-PD-1 antibody, wherein glycosylation may occur to at least one hydroxyamino acid residue contained in the light chain. By way of non-limiting example, the glycosylation may occur to at least one hydroxyamino acid residue contained in the light chain variable region. By way of non-limiting example, the glycosylation may occur to at least one serine (Ser) or threonine (Thr) residue contained in the light chain variable region.

In one embodiment, the antibody is a rituximab antibody, wherein glycosylation may occur to at least one hydroxyamino acid residue contained in the light chain. By way of non-limiting example, the glycosylation may occur to at least one hydroxyamino acid residue contained in the light chain variable region. By way of non-limiting example, the glycosylation may occur to at least one serine (Ser) or threonine (Thr) residue contained in the light chain variable region. Still by way of non-limiting example, the glycosylation may occur to at least one hydroxyamino acid residue contained in the light chain represented by SEQ ID NO: 6. Still by way of non-limiting example, the glycosylation may occur to at least one hydroxyamino acid residue contained the light chain variable region represented by SEQ ID NO: 4.

In one embodiment, the antibody is a rituximab antibody, wherein the glycosylation may occur to at least one hydroxyamino acid residue at the $7^{th}$, $12^{th}$, $14^{th}$, $26^{th}$, $51^{st}$, $55^{th}$, $62^{nd}$, $101^{st}$, $155^{th}$, or $181^{st}$ position from the 5' end of the light chain. By way of non-limiting example, the glycosylation may occur to at least one of serine residues at the $7^{th}$, $12^{th}$, $14^{th}$, $26^{th}$, and $62^{nd}$ positions from the 5' end of the light chain variable region. By way of non-limiting example, the glycosylation may occur to at least one of serine residues at the $7^{th}$, $12^{th}$, and $14^{th}$ positions from the 5' end of the light chain variable region.

In one embodiment, the antibody is a nivolumab antibody, wherein glycosylation may occur to at least one hydroxyamino acid residue contained in the light chain. By way of non-limiting example, the glycosylation may occur to at least one hydroxyamino acid residue contained in the light chain variable region. By way of non-limiting example, the glycosylation may occur to at least one serine (Ser) or threonine (Thr) residue contained in the light chain variable region. Still by way of non-limiting example, the glycosylation may occur to at least one hydroxyamino acid residue contained in the light chain represented by SEQ ID NO: 10. Still by way of non-limiting example, the glycosylation may occur to at least one hydroxyamino acid residue contained the light chain variable region represented by SEQ ID NO: 8.

In one embodiment, the antibody is a nivolumab antibody, wherein glycosylation may occur to at least one of serine residues at the $7^{th}$, $12^{th}$, and $14^{th}$ positions from the 5' end of the light chain variable region.

In one embodiment, the antibody is a pembrolizumab antibody, wherein glycosylation may occur to at least one hydroxyamino acid residue contained in the light chain. By way of non-limiting example, the glycosylation may occur to at least one hydroxyamino acid residue contained in the light chain variable region. By way of non-limiting example, the glycosylation may occur to at least one serine (Ser) or threonine (Thr) residue contained in the light chain variable region. Still by way of non-limiting example, the glycosylation may occur to at least one hydroxyamino acid residue contained in the light chain represented by SEQ ID NO: 14. Still by way of non-limiting example, the glycosylation may occur to at least one hydroxyamino acid residue contained the light chain variable region represented by SEQ ID NO: 12.

In one embodiment, the antibody is a pembrolizumab antibody, wherein glycosylation may occur to at least one of serine residues at the $7^{th}$, $12^{th}$, and $14^{th}$ positions from the 5' end of the light chain variable region.

In one embodiment, the antibody is a pidilizumab antibody, wherein glycosylation may occur to at least one hydroxyamino acid residue contained in the light chain. By way of non-limiting example, the glycosylation may occur to at least one hydroxyamino acid residue contained in the light chain variable region. By way of non-limiting example, the glycosylation may occur to at least one serine (Ser) or threonine (Thr) residue contained in the light chain variable region. Still by way of non-limiting example, the glycosylation may occur to at least one hydroxyamino acid residue contained in the light chain represented by SEQ ID NO: 18.

Still by way of non-limiting example, the glycosylation may occur to at least one hydroxyamino acid residue contained the light chain variable region represented by SEQ ID NO: 16.

In one embodiment, the antibody is a pidilizumab antibody, wherein glycosylation may occur to at least one of serine residues at the $7^{th}$, $12^{th}$, and $14^{th}$ positions from the 5' end of the light chain variable region.

In one embodiment, the glycosylation may be O-linked glycosylation. By way of non-limiting example, N-acetylglucosamine may be bound to at least one hydroxyamino acid residue contained in the light chain or the light chain variable region of an anti-CD20 antibody or anti-PD-1 antibody.

By way of non-limiting example, for the O-linked glycosylation in an anti-CD20 antibody or anti-PD-1 antibody, O-GlcNAc transferase (OGT) may be used to allow N-acetylglucosamine to bind to the hydroxyamino acid residue in the light chain or the light chain variable region. The systematic name of the O-GlcNAc transferase is "UDP-N-acetyl-D-glucosamine:protein-O-β-N-acetyl-D-glucosamine transferase". In humans, this enzyme is encoded by OGT gene.

By way of non-limiting example, the O-linked glycosylation may be achieved using an O-GlcNAcase inhibitor (OGA inhibitor). By way of non-limiting example, an O-GlcNAcase inhibitor may be Thiamet-G, streptozotocin (STZ), PUGNAc, NAG-thiazoline, NButGT, (2R,3S)-iminocyclitol, PUGNAc-imidazole hybrid, or GlcNAcstatin C. By way of non-limiting example, an O-GlcNAcase inhibitor is Thiamet-G. By way of non-limiting example, the O-linked glycosylation may be achieved by adding an O-GlcNAcase inhibitor to the culture medium of a host cell producing each antibody.

By way of non-limiting example, a glycosyl linking group of N-acetylglucosamine may be further added when the antibody-producing host cell is cultured for O-linked glycosylation in the light chain of an anti-CD20 antibody or anti-PD-1 antibody.

Another aspect of the present disclosure provides a method of producing an antibody by glycosylating at least one hydroxyamino acid residue in the light chain thereof.

In one embodiment, for O-linked glycosylation, a step of preparing an antibody may be carried out first. In one embodiment, the antibody may contain a hydroxyamino acid residue, which is an amino acid residue having a hydroxyl group, in the light chain. By way of non-limiting example, the antibody may contain a hydroxyamino acid residue in the light chain variable region. By way of non-limiting example, the hydroxyamino acid residue is serine (Ser), threonine (Thr), or tyrosine (Tyr). By way of non-limiting example, the hydroxyamino acid residue is a serine (Ser) or threonine (Thr) residue.

In one embodiment, the antibody may contain at least one hydroxyamino acid residue at one of the $7^{th}$, $12^{th}$, $14^{th}$, $26^{th}$, $51^{st}$, $55^{th}$, $62^{nd}$, $101^{st}$, $155^{th}$, and $181^{st}$ positions from the 5' end of the light chain. By way of non-limiting example, the at least one hydroxyamino acid residue is in the light chain variable region.

In one embodiment, the antibody may contain at least one hydroxyamino acid residue at one of the $7^{th}$, $12^{th}$, and $14^{th}$ positions from the 5' end of the light chain. By way of non-limiting example, the at least one hydroxyamino acid residue is in the light chain variable region.

In one embodiment, the method may further comprise transforming a host cell with a recombinant nucleic acid molecule that encodes the antibody, and culturing the transformed host cell to produce the antibody.

In one embodiment, the antibody may be an anti-CD20 antibody or an anti-PD-1 antibody.

By way of non-limiting example, the anti-CD20 antibody may be a type I chimeric anti-CD20 antibody, including but not limited to rituximab, HI47 IgG3 (ECACC, hybridoma), 2C6 IgG1 (as disclosed in WO 2005/103081), 2F2 IgG1 (as disclosed in WO 2004/035607 and WO 2005/103081), or 2H7 IgG1 (as disclosed in WO 2004/056312). By way of non-limiting example, the anti-CD20 antibody may be a rituximab antibody.

In one embodiment, to prepare a rituximab antibody, a host cell, transformed with at least one recombinant nucleic acid molecule that encodes rituximab, may be prepared and cultured. In one embodiment, a host cell, transformed with at least one recombinant nucleic acid molecule that encodes a human immunoglobulin G1 (IgG1) heavy chain constant region represented by SEQ ID NO: 1; a human kappa light chain constant region represented by SEQ ID NO: 2; a murine heavy chain variable region represented by SEQ ID NO: 3; and a murine light chain variable region represented by SEQ ID NO: 4, may be prepared and cultured. In one embodiment, a host cell, transformed with at least one recombinant nucleic acid molecule that encodes a heavy chain represented by SEQ ID NO: 5 and a light chain represented by SEQ ID NO: 6, may be prepared and cultured.

By way of non-limiting example, the anti-PD-1 antibody may be nivolumab, pembrolizumab, pidilizumab, AMP 514 (Amplimmune), PDR-001 (Novartis), MEDI-0690 (also known as AMP-514) (MedImmune LLC), SHR-1210 (Incyte Corp.), REGN-2810 (Regeneron Pharmaceuticals, Inc.), PF-06801591 (Pfizer), TSR-042 (also known as ANB011) (Tesaro, Inc.), BGB-A317 (BeiGene, Ltd.), or JS001 (Shanghai Junshi Bioscience Co., Ltd.). By way of non-limiting example, the anti-PD-1 antibody may be a nivolumab, pembrolizumab, or pidilizumab antibody.

In one embodiment, to prepare a nivolumab antibody, a host cell, transformed with at least one recombinant nucleic acid molecule that encodes nivolumab, may be prepared and cultured. In one embodiment, a host cell, transformed with at least one recombinant nucleic acid molecule that encodes a heavy chain variable region represented by SEQ ID NO: 7 and a light chain variable region represented by SEQ ID NO: 8, may be prepared and cultured. In one embodiment, a host cell, transformed with at least one recombinant nucleic acid molecule that encodes a heavy chain represented by SEQ ID NO: 9 and a light chain represented by SEQ ID NO: 10, may be prepared and cultured.

In one embodiment, to prepare a pembrolizumab antibody, a host cell, transformed with at least one recombinant nucleic acid molecule that encodes pembrolizumab, may be prepared and cultured. In one embodiment, a host cell, transformed with at least one recombinant nucleic acid molecule that encodes a heavy chain variable region represented by SEQ ID NO: 11 and a light chain variable region represented by SEQ ID NO: 12, may be prepared and cultured.

In one embodiment, a host cell, transformed with at least one recombinant nucleic acid molecule that encodes a heavy chain represented by SEQ ID NO: 13 and a light chain represented by SEQ ID NO: 14, may be prepared and cultured.

In one embodiment, to prepare a pidilizumab antibody, a host cell, transformed with at least one recombinant nucleic acid molecule that encodes pidilizumab, may be prepared and cultured. In one embodiment, a host cell, transformed with at least one recombinant nucleic acid molecule that encodes a heavy chain variable region represented by SEQ ID NO: 15 and a light chain variable region represented by SEQ ID NO: 16, may be prepared and cultured. In one embodiment, a host cell, transformed with at least one recombinant nucleic acid molecule that encodes a heavy chain represented by SEQ ID NO: 17 and a light chain represented by SEQ ID NO: 18, may be prepared and cultured.

In one embodiment, the host cell may be a cell of mammalian, plant, insect, fungal, or bacterial origin. By way of non-limiting example, the host cell is a mammalian cell. The mammalian host cell suitable for expressing the antibody described above and herein includes, but is not limited to, Chinese hamster ovary (CHO) cells (including dhfr(−) CHO cells used with DHFR selection markers), NS0 myeloma cells, COS cells, SP2 cells, monkey kidney CV1 cells, human embryonic kidney cell line 293, baby hamster kidney cells (BHK), mouse Sertoli cells (TM4), African green monkey kidney cells (VERO-76), human cervical cancer cells (HELA), canine kidney cells (MDC), buffalo rat liver cells (BRL 3A), human lung cells (W138), human liver cells (Hep G2), mouse breast cancer cells (MMT 060562), TRI cells, MRC 5 cells, and FS4 cells. By way of non-limiting example, the host cell may be derived from a rodent including, but not limited to, a Chinese hamster ovary (CHO) cell. By way of non-limiting example, the rodent host cell may be a CHO-K1 cell, and/or a culture medium used may be a serum-free medium suitable for CHO-K1 cell growth. By way of non-limiting example, the culture medium may be prepared using the product Sigma #14360C (EX-CELL® CD CHO Serum-Free Medium for CHO Cells, Chemically Defined).

In one embodiment, the host cell may be transformed, i.e., genetically modified, with at least one recombinant nucleic acid molecule, such as an expression vector, capable of stably producing a recombinant protein. In one embodiment, the host cell may be transformed with one recombinant nucleic acid molecule that encodes both the heavy and light chains of the antibody, or two recombinant nucleic acids, one encoding the light chain of the antibody and the other encoding the heavy chain of the antibody. In one embodiment, a recombinant antibody may be produced from one recombinant nucleic acid molecule that encodes both the heavy and light chains of the antibody. In one embodiment, a recombinant antibody may be produced from one recombinant nucleic acid molecule, and expression of the heavy and light chains may be controlled by separate promoters which can be the same or different. In one embodiment, a recombinant antibody may be produced from one recombinant nucleic acid molecule, and expression of the heavy and light chains may be controlled by separate promoters which are the same.

As used herein, the term "vector" is a nucleic acid molecule that is capable of transporting another nucleic acid linked thereto. One type of vector is a "plasmid," which refers to circular double-stranded DNA into which additional DNA segments can be ligated. Another type of vector is a phage vector. Yet another type of vector is a viral vector, in which additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thus replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. As used herein, "plasmid" and "vector" may be used interchangeably as the plasmid is the most commonly used form of vector.

By way of non-limiting example, a suitable expression vector may be a commercially widely used pCDNA vector, F, R1, RP1, Col, pBR322, ToL, Ti vector; cosmid; phage such as lambda, lambdoid, M13, Mu, p1 P22, Qμ, T-even, T2, T3, T7; or plant virus. Any expression vector known to those skilled in the art as an expression vector can be used herein, and the selection of an expression vector depends on the nature of the target host cell. Introduction of a vector into a host cell may be performed by, but is not limited to, calcium phosphate transfection, viral infection, DEAE-dextran-mediated transfection, lipofectamine transfection, or electroporation. In one embodiment, the vector may contain at least one selection marker or no selection marker, depending on whether or not a product is produced. In one embodiment, the selection marker is selected depending on the target host cell, which is done using methods already known in the art.

To facilitate purification of the antibody, a tag sequence may be inserted and fused to an expression vector. The tag includes, but is not limited to, hexa-histidine tag, hemagglutinin tag, myc tag, and flag tag. Any other tags known in the art to facilitate purification can be used herein.

The culture medium used for culturing the host cell is a solution containing nutrients required for growing mammalian cells. Typically, the nutrients include essential and non-essential amino acids, vitamins, energy sources, lipids, and trace elements required by the cells for minimal growth and/or survival. In one embodiment, the medium is chemically defined in that all components and their concentrations are known. By way of non-limiting example, the medium may be serum-free, which does not contain hydrolysates or any animal-derived component. Still by way of non-limiting example, the medium may be serum-free, which does not contain hydrolysates or any animal-derived component, but contains some chemicals required for the separation process.

In one embodiment, the glycosylation is O-linked glycosylation and N-acetylglucosamine may be bound to at least one hydroxyamino acid residue contained in the light chain or the light chain variable region of the antibody.

In one embodiment, in a case where the antibody expressed during the culturing of the host cell is an anti-CD20 antibody or an anti-PD-1 antibody, an O-GlcNAcase inhibitor (OGA inhibitor) may be added in order to cause at least one hydroxyamino acid residue contained in the light chain to undergo O-linked glycosylation.

In one embodiment, the OGA inhibitor may be selected from the group consisting of Thiamet-G, streptozotocin (STZ), PUGNAc, NAG-thiazoline, NButGT, (2R,3 S)-iminocyclitol, PUGNAc-imidazole hybrid, and GlcNAcstatin C. By way of non-limiting example, the OGA inhibitor is Thiamet-G.

In one embodiment, the O-linked glycosylation may occur to at least one of the following hydroxyamino acid residues: a hydroxyamino acid residue at the $7^{th}$, $12^{th}$, $14^{th}$, $26^{th}$, $51^{st}$, $55^{th}$, $62^{nd}$, $101^{st}$, $155^{th}$, or $181^{st}$ position of the light chain. By way of non-limiting example, the O-linked glycosylation may occur to at least one hydroxyamino acid residue at the $7^{th}$, $12^{th}$, $14^{th}$, $26^{th}$, and $62^{nd}$ positions, and or at least one hydroxyamino acid residue at the $7^{th}$, $12^{th}$, and $14^{th}$ positions, from the 5' end of the light chain.

In one embodiment, for a rituximab antibody, the O-linked glycosylation may occur to at least one serine residue at the $7^{th}$, $12^{th}$, $14^{th}$, $26^{th}$, $51^{st}$, $55^{th}$, $62^{nd}$, $101^{st}$, $155^{th}$, and $181^{st}$ positions from the 5' end of the light chain. By way of non-limiting example, the O-linked glycosylation may occur to at least one serine residue at the $7^{th}$, $12^{th}$, $14^{th}$, $26^{th}$, and $62^{nd}$ positions from the 5' end of the light chain variable region.

In one embodiment, for a nivolumab antibody, the O-linked glycosylation may occur to at least one serine residue at the $7^{th}$, $12^{th}$, and $14^{th}$ from the 5' end of the light chain. By way of non-limiting example, the O-linked glycosylation may occur to at least one serine residue at the $7^{th}$, $12^{th}$, and $14^{th}$ from the 5' end of the light chain variable region.

In one embodiment, for a pembrolizumab antibody, the O-linked glycosylation may occur to at least one serine residue at the $7^{th}$, $12^{th}$, and $14^{th}$ from the 5' end of the light chain. By way of non-limiting example, the O-linked glycosylation may occur to at least one serine residue at the $7^{th}$, $12^{th}$, and $14^{th}$ from the 5' end of the light chain variable region.

In one embodiment, for a pidilizumab antibody, the O-linked glycosylation may occur to at least one serine residue at the $7^{th}$, $12^{th}$, and $14^{th}$ from the 5' end of the light chain. By way of non-limiting example, the O-linked glycosylation may occur to at least one serine residue at the $7^{th}$, $12^{th}$, and $14^{th}$ from the 5' end of the light chain variable region.

In one embodiment, for O-linked glycosylation of an anti-CD20 antibody or anti-PD-1 antibody, O-GlcNAc transferase (OGT) may be additionally added when the host cell is cultured, so that N-acetylglucosamine binds to a hydroxyamino acid residue in the light chain or light chain variable region of the anti-CD20 antibody or anti-PD-1 antibody.

In one embodiment, for O-linked glycosylation in the light chain of an anti-CD20 antibody or anti-PD-1 antibody, a glycosyl linking group of N-acetylglucosamine may be further added when the host cell is cultured.

An O-linked glycosylated antibody may be produced according to any of the methods disclosed above and herein and subsequently harvested. Because the O-linked glycosylated antibody, which is a recombinant protein expressed from a mammalian cell, is typically secreted into a cell culture medium during a culturing process, harvesting of the product is achieved by separating the cell culture medium containing the O-linked glycosylated antibody from the cells at the end of the culturing process. The cell separation method should be gentle so that cell destruction is minimized to prevent increased cell debris, which in turn may affect the quality of the antibody product, and the release of proteases and other molecules. In general, harvesting of a cell culture medium, which contains a recombinant protein such as an O-linked glycosylated antibody, involves centrifugation and/or filtration, whereby the recombinant protein can be present in the supernatant and/or the filtrate. Expanded bed adsorption chromatography can be an alternative to avoid centrifugation/filtration methods.

Once harvested, the O-linked glycosylated antibody can be purified from the cell culture medium. Purification of the O-linked glycosylated antibody may generally be achieved by a series of chromatographic steps including, but not limited to, anion exchange chromatography, cation exchange chromatography, affinity chromatography, hydrophobic interaction chromatography, hydroxyapatite chromatography, and size exclusion chromatography. In addition, the purification process may include at least one ultrafiltration, nanofiltration, or diafiltration step. Suitable methods include, but are not limited to, steps of anion exchange chromatography in flow-through mode, affinity chromatography on Protein A resin, and cation exchange chromatography in bind-and-elute mode (see, PCT/EP2015/054862).

The methods disclosed above and herein can be used to produce O-linked glycosylated antibodies on a large scale that corresponds to a culture volume of at least 500 or 1,000 liters, at least 5,000 or 8,000 liters, or at least 10,000 or 20,000 liters.

Yet another aspect of the present disclosure provides a method of preventing or treating a proliferative disease in a subject in need thereof by administering to the subject a therapeutically effective amount of the glycosylated antibody described above or herein. In one embodiment, the glycosylated antibody may exist in a pharmaceutical composition as an active ingredient.

Among the glycosylated antibodies provided herein, the anti-CD20 antibody or anti-PD-1 antibody, obtained by causing a specific hydroxyamino acid residue to undergo O-linked glycosylation in the light chain thereof, can exhibit a remarkably increased productivity while maintaining its titer at an equivalent level to or higher than the original antibody.

In one embodiment, the proliferative disease is a cancer. A "cancer" typically refers to or indicates a physiological condition characterized by unregulated cell growth in mammals. By way of non-limiting example, the cancer that may be prevented or treated using the glycosylated antibody described above and herein, depending on the development site thereof, includes, but is not limited to, pancreatic cancer, thyroid cancer, breast cancer, biliary tract cancer, gallbladder cancer, colorectal cancer, uterine cancer, esophageal cancer, gastric cancer, brain cancer, rectal cancer, lung cancer, bladder cancer, kidney cancer, ovary cancer, prostate cancer, uterine cancer, head and neck cancer, skin cancer, blood cancer, and liver cancer. By way of non-limiting example, the cancer may be a blood cancer, melanoma, lung cancer, kidney cancer, head and neck cancer, or gastric cancer.

As used herein, "prevention" or "preventing" may include, without limitation, any act of blocking symptoms of cancer, or suppressing or delaying the symptoms, using the pharmaceutical composition or antibody disclosed above and herein.

As used herein, "treatment" or "treating" may include, without limitation, any act of ameliorating or beneficially altering symptoms of cancer, using the pharmaceutical composition or antibody disclosed above and herein.

In one embodiment, the pharmaceutical composition or antibody may be further co-administered with other anti-cancer agents, so that a growth inhibitory effect on cancer cells can be further enhanced.

By way of non-limiting example, an anti-cancer agent may be selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminoglutethimide, anagrelide, navelbine, fadrozole, tamoxifen, toremifene, testolactone, anastrozole, letrozole, vorozole, bicalutamide, lomustine and carmustine.

In one embodiment, the pharmaceutical composition or antibody may be characterized by being in the form of capsules, tablets, granules, injections, ointments, powders, or beverages, and the pharmaceutical composition may be characterized by being targeted to humans.

In one embodiment, the pharmaceutical composition or antibody may be formulated in the form of oral preparations such as powders, granules, capsules, tablets, and aqueous suspensions, or in the form of preparations for external use, suppositories, and sterile injectable solutions, according to conventional methods. In one embodiment, the pharmaceutical composition may further comprise a pharmaceutically acceptable carrier. By way of non-limiting example, a pharmaceutically acceptable carrier may be a binder, a glidant, a disintegrant, an excipient, a solubilizer, a dispersant, a stabilizer, a suspending agent, a pigment, a flavor, a buffer, a preserving agent, a pain-relieving agent, an isotonic agent, a base, or a lubricant, which can be used for oral administration, for injections, or for topical administration. The pharmaceutical composition may be prepared in various ways depending on the route of administration. By way of non-limiting example, the pharmaceutical composition may be formulated in the form of pills, tablets, troches, capsules, elixirs, suspensions, syrups, gels, slurries, wafers, or the like for oral administration, or formulated in the form of unit dosage ampoules or multiple dosage forms for injections. In one embodiment, the pharmaceutical composition may be formulated into solutions, suspensions, tablets, capsules, sustained-release preparations, or the like.

Meanwhile, as examples of carriers, diluents, or excipients suitable for making the pharmaceutical preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

For the prevention or treatment of a proliferative disease, the pharmaceutical composition or antibody may be administered through oral, intravenous, intramuscular, intra-arterial, intramedullary, intradural, intracardiac, transdermal, subcutaneous, intraperitoneal, intranasal, intestinal, topical, sublingual, or rectal route. By way of the non-limiting example, the pharmaceutical composition or antibody is administered through oral or parenteral route. As used herein, "parenteral" route includes subcutaneous, intradermal, intravenous, intramuscular, intra-articular, intrabursal, intrasternal, intradural, intralesional, and intracranial injection or infusion techniques. Alternatively, the pharmaceutical composition or antibody may be administered in the form of suppositories for rectal administration.

When administering the pharmaceutical composition or antibody described above and herein to a patient, a variety of factors need to be considered, including, but not limited to, activity of a certain compound used, the patient's age, body weight, general health status, sex, diet, time of administration, route of administration, rate of excretion, drug combination, and severity of the disease to be prevented or treated. Also, the dosage may vary depending on the patient's condition, body weight, severity of disease, drug form, route of administration, and duration. By way of non-limiting example, the pharmaceutical composition or antibody may be administered in an amount of 0.0001 to 50 mg/kg of body weight or 0.001 to 50 mg/kg of body weight per day. It may be administered once a day or several times a day.

When administered alone, route of administration of the glycosylated antibody may be determined based on the patient's size and condition according to standard pharmaceutical practice. By way of non-limiting examples, the antibody may be administered through intravenous, intra-arterial, intraperitoneal, intrapulmonary, intravascular, intramuscular, intra-tracheal, subcutaneous, intraocular, intrathecal, or transdermal route.

As to the dosage of the antibody for administration, it varies depending on the specific type of the antibody to be administered, the route of administration, and the specific type and stage of proliferative disease to be treated. A sufficient amount/dose is considered as one that brings about a desired response, such as a therapeutic response to cancer, without severe toxicity or adverse events. In one embodiments, the dose of a glycosylated antibody to be administered is a therapeutically effective amount. In one embodiments, the dose of a glycosylated antibody is an amount sufficient to reduce the tumor size, the number of cancer cells, or the tumor growth rate, by at least about 10%, 20%, 30%, 40%, 50%, 60%, 70%, 80%, 90%, 95%, or 100%, as compared with the corresponding tumor size, number of cancer cells, or tumor growth rate in the same individual before the treatment, or the corresponding activity in another individual having not received the treatment. Standard methods, such as in vitro assays, cell-based assays, animal models, or human experiments, using purified enzymes may be used to determine the scale of effects.

The glycosylated antibody described above and herein may be administered alone or in combination with any other therapy, such as surgery, radiation therapy, gene therapy, immunotherapy, bone marrow transplantation, stem cell transplantation, hormone therapy, targeted therapy, cryotherapy, ultrasound therapy, photodynamic therapy, and chemotherapy. Additionally, an individual at a greater risk of developing a proliferative disease may receive treatment to prevent and/or delay onset of the disease.

Hereinafter, the present disclosure will be described in more detail by way of examples. These examples are provided by way of illustration and not by way of limitation.

Example 1: Antibody Production

Antibody and Glycosylation Enzyme Cloning: for the sequence of rituximab, reference can be made to Drugbank (https://www.drugbank.ca). The heavy (SEQ ID NO: 5) and light (SEQ ID NO: 6) chains of rituximab were prepared through DNA synthesis, provided that the heavy chain constant region was obtained through PCR from the DNA of a healthy donor.

Lentivirus Production: HEK293T cells were co-transfected with the antibody clonal DNA prepared above and the lentiviral constituent DNA, and culture was performed. After overnight culture, replacement of the cell culture medium was performed. When 24 hours elapsed, the cell culture medium was taken and centrifuged at 1000 rcf for 3 minutes at 4° C. Only the supernatant was transferred separately into a clean tube, and then the cells mixed with the cell culture medium were removed. The resultant was stored at −70° C.

Antibody Production: CHO-K1 cells were inoculated into a 12-well plate at $1\times10^5$ cells/well and then cultured. The next day, the culture medium having lentivirus-containing cells and a fresh culture medium were mixed at a ratio of 1:1, and treatment with this mixture was performed. Culture was performed for 24 hours. The culture medium was replaced with a new medium, and then treatment with puromycin and blasticidin at 10 μg/ml each was performed for selection. When 72 hours elapsed, the remaining cells were proliferated to obtain sufficient cells. For the cells thus obtained, the culture medium was replaced with a serum-free medium (EX-CELL CD CHO Serum-Free Medium for CHO Cells, Chemically Defined, Sigma, 14360C), and then treatment with Thiamet-G (Sigma Cat #SML0244) reagent at a concentration of 30 μM was performed. The cells were cultured in a $CO_2$ incubator at 30° C. for 2 weeks. Then, the culture medium was collected and centrifuged at 1000 rcf for 3 minutes at 4° C. Only the supernatant was transferred separately into a clean tube, and the cells mixed with the supernatant were removed. The resultant was stored at 4° C.

Antibody Purification: the antibody-containing culture medium was treated with protein A agarose beads (Pierce Protein A Agarose, Therm Fisher Scientific, QE218104), and the reaction was allowed to proceed at 4° C. for 4 hours. The supernatant was removed by centrifugation, and washing with a washing buffer (0.1 M NaPO₄, 0.15 M NaCl, pH 7.4) was performed five times. For the beads from which the supernatant was removed, elution was again performed 5 times with an elution buffer (0.2 M glycine, pH 3) in the same bead volume. The eluted portion was collected in centrifugal filter units (Amicon Ultra-4, Millipore, #UFC800324), and the buffer was replaced with PBS over three times for 1 hour each at 13200 rpm. Then, the total protein was quantified by the Bradford method.

Example 2: Identification of Changes in Antibody Production after Glycosylation

To identify changes in antibody production when Thiamet-G caused rituximab to undergo O-linked glycosylation in Example 1, production of the purified antibody was measured in a case where Thiamet-G was added and a case where Thiamet-G was not added. As illustrated in FIG. 1, it was found that as compared with a case where no treatment was performed, the antibody production increased about 2 times in a case where Thiamet-G was added for O-linked glycosylation of rituximab.

Figure 2:
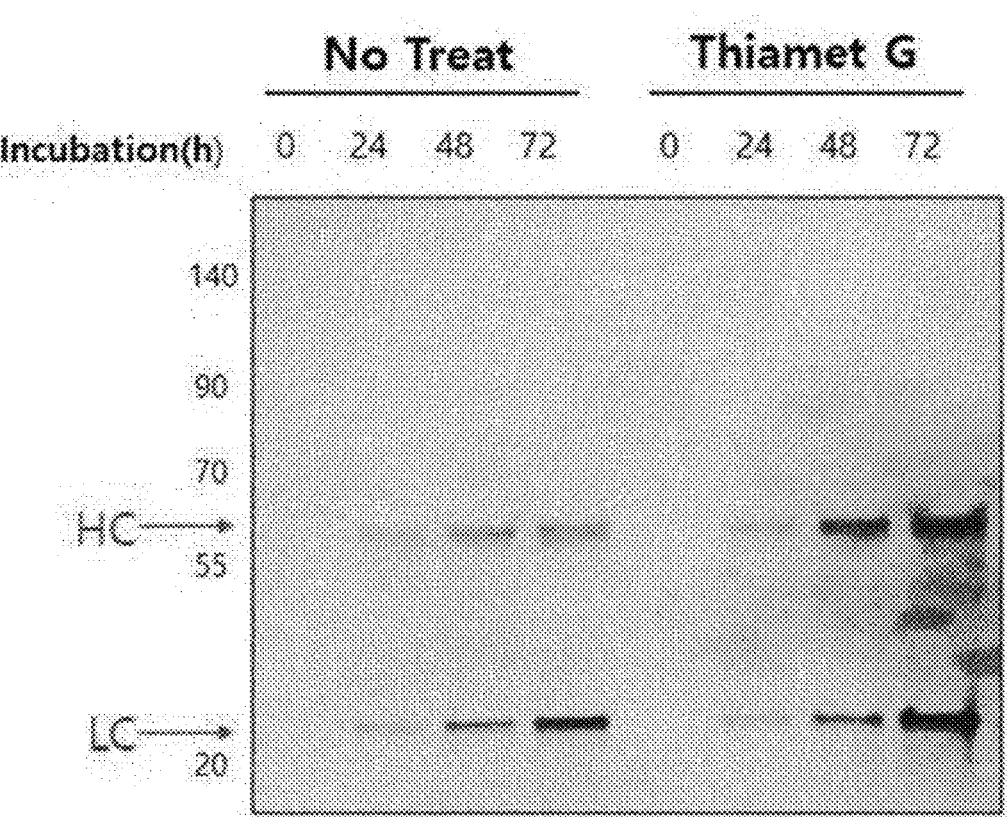
FIG. 2 illustrates results obtained by analyzing, through Western blotting, changes in expression level of the heavy and light chains of a rituximab antibody over time after addition of Thiamet-G.
Figure 3A:
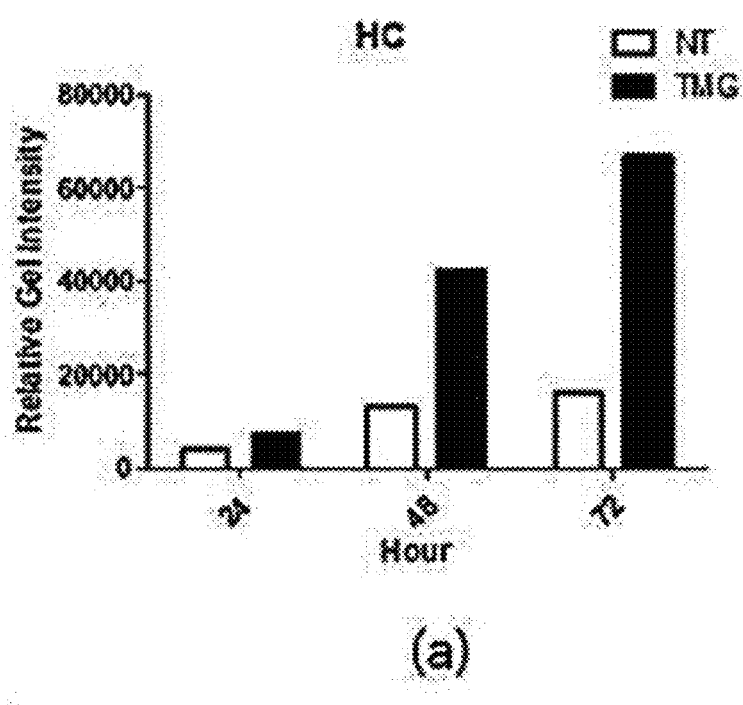
FIGS. 3A-3B graphically illustrate changes in expression level of the heavy chain (FIG. 3A) and light chain (FIG. 3B) of a rituximab antibody over time after addition of Thiamet-G.
Figure 3B:
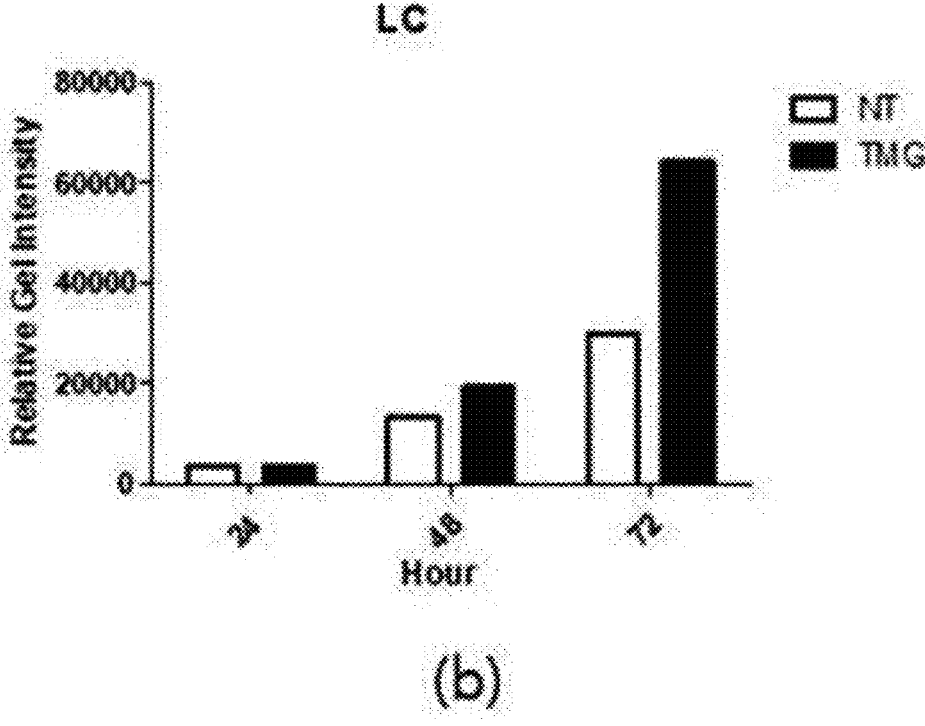

To identify changes in protein amount of heavy and light chains of antibody caused by treatment with Thiamet-G, the following experiment was performed to check changes in antibody production over time after addition of Thiamet-G. The cell culture medium was collected when 24 hours, 48 hours, and 72 hours elapsed after addition of Thiamet-G at a concentration of 30 μM. The collected culture medium was subjected to electrophoresis on an equal volume of acrylamide gel so that proteins were separated by size, and then the proteins were transferred to a nitrocellulose membrane (NC membrane). Portions other than the proteins electrically transferred to the nitrocellulose membrane were blocked with TBS-T containing 5% non-fat milk and 0.1% Tween 20 at room temperature for 1 hour. Incubation with anti-human-HRP and anti-mouse-HRP antibodies was performed at room temperature for 30 minutes, and then washing with TBS-T was performed three times for 10 minutes each. The ECL solution was used to sensitize an x-ray film (FIG. 2), and production of the heavy and light chains at each time point was analyzed (FIG. 3). As a result, it was found that the production of the heavy and light chains of the antibody remarkably increased over time in a case of being treated with Thiamet-G.

Figure 4:
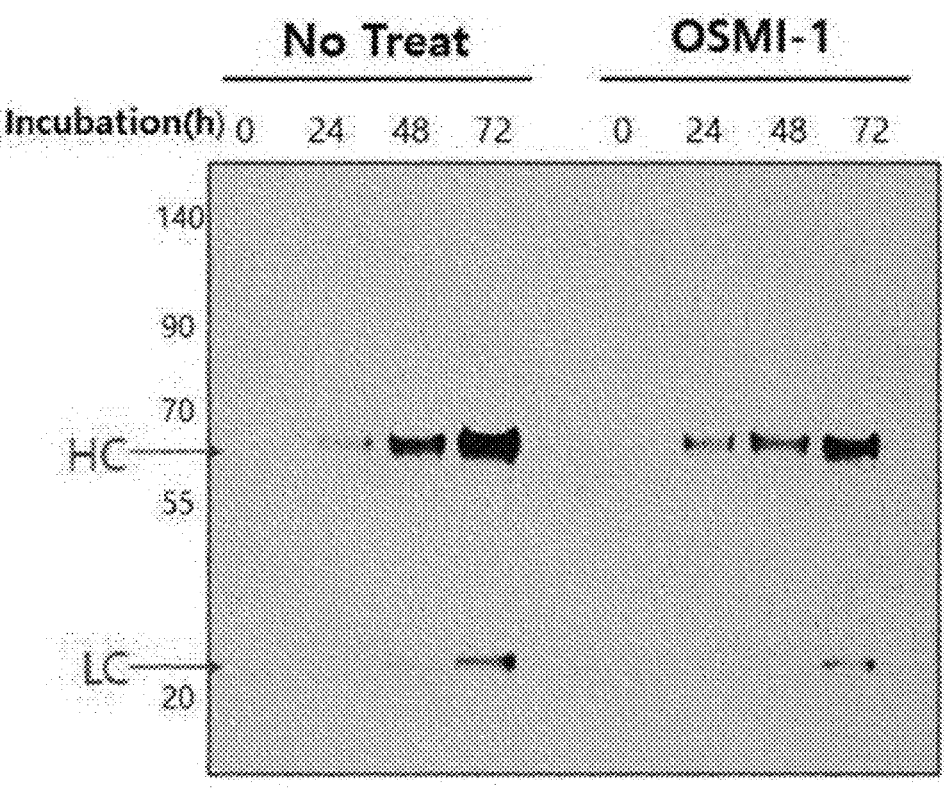
FIG. 4 illustrates results obtained by analyzing, through Western blotting, changes in expression level of the heavy and light chains of a rituximab antibody over time after addition of OSMI-1.
Figure 5:
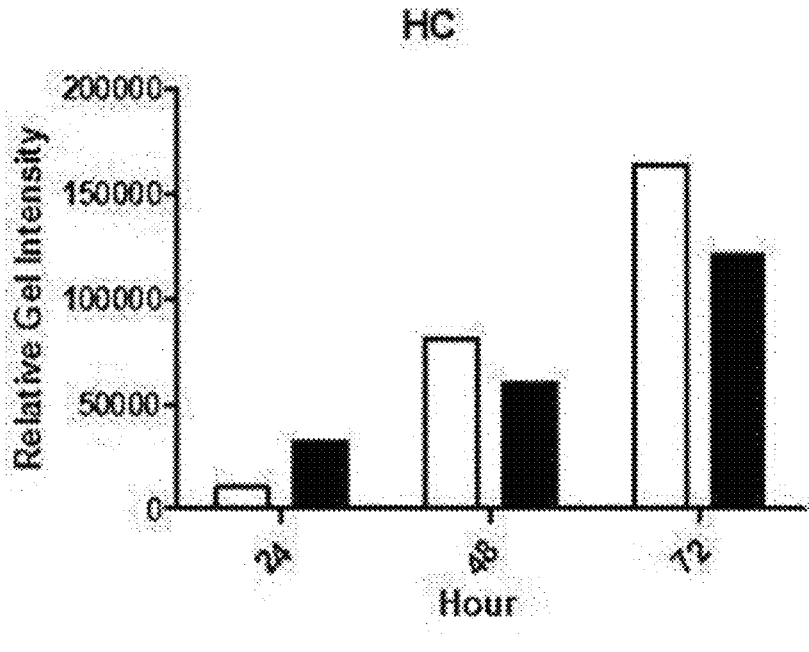
FIG. 5 graphically illustrates changes in expression level of the heavy chain of a rituximab antibody over time after addition of OSMI-1.

To identify whether the increased antibody production observed above was caused by O-linked glycosylation of rituximab, as a comparative example, the following experiment was performed to identify changes in protein amount of heavy and light chains of antibody caused by OSMI (drug that acts opposite to Thiamet-G). During the antibody production process, the reagent OSMI-1 (Sigma #SML1621), which corresponds to an OGT inhibitor, at a concentration of 30 μM was added in place of Thiamet-G. Then, in the same manner as described above, the cell culture medium was collected when 24 hours, 48 hours, and 72 hours elapsed, and the production of the antibody and its heavy chain was analyzed through Western blotting (FIGS. 4-5). As a result, it was found that even in a case of being treated with OSMI-1, production of the heavy and light chains of the antibody increased over time, but the extent of increase in production decreased as compared with the untreated negative control.

Figure 6A:
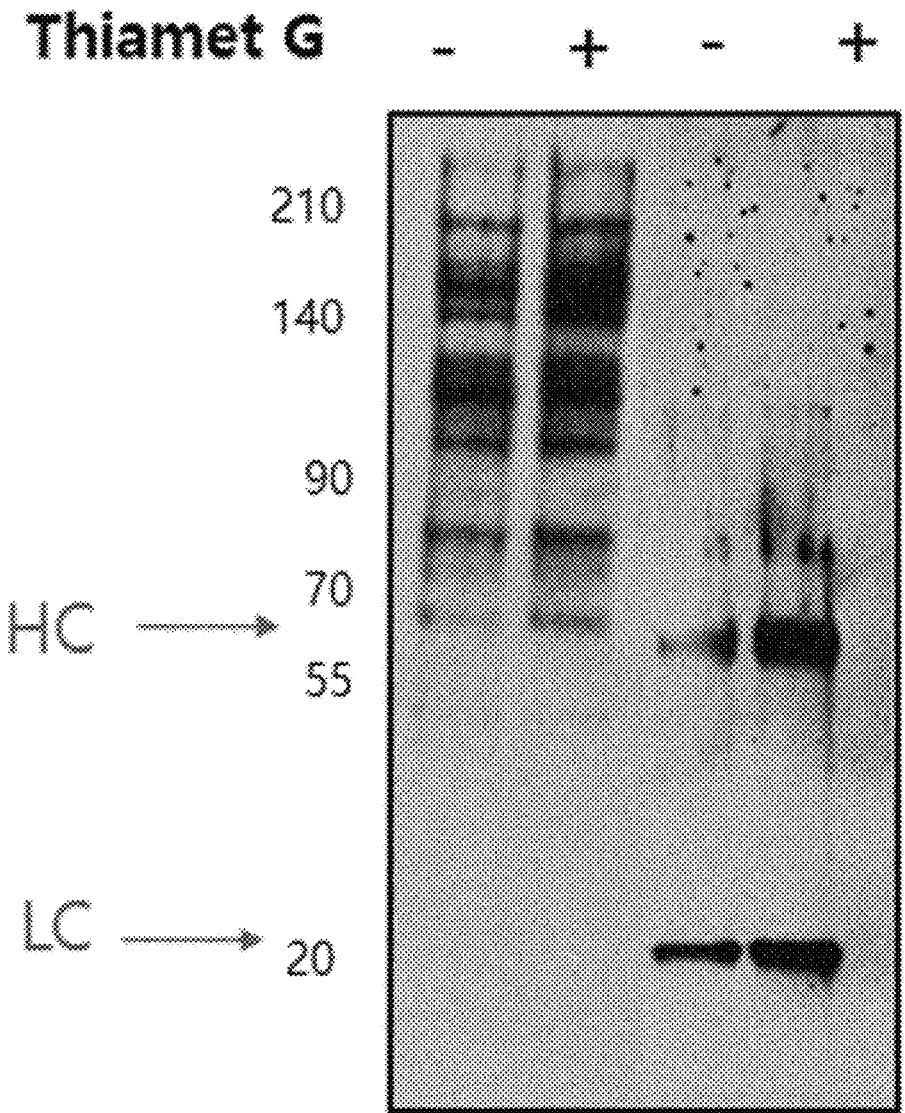
FIG. 6A illustrates results obtained by analyzing, through Western blotting using an O-linked N-acetylglucosamine-specific antibody (RL2), the degree of binding of O-linked N-acetylglucosamine (O-GlcNAc) in various proteins, which are in a host cell lysate (CHO-RTX Lysate), and a rituximab antibody isolated and purified from the lysate in a case where Thiamet G is added and a case where Thiamet G is not added.

Example 3: Identification of Differences in Degree of Binding of O-GlcNAc in Antibody Based on the total protein amount, the isolated rituximab was subjected to electrophoresis on acrylamide gel so that proteins were separated by size. Then, the proteins were transferred to a nitrocellulose membrane. Portions other than the proteins electrically transferred to the nitrocellulose membrane were blocked with TBS-T containing 5% non-fat milk and 0.1% Tween 20 at room temperature for 1 hour. Incubation with O-linked N-acetylglucosamine (O-GlcNAc)-specific antibody (RL2-HRP) was performed at room temperature for 1 hour, and then washing with TBS-T was performed three times for 10 minutes each. The ECL solution was used to sensitize an x-ray film (FIG. 6A).

Figure 6B:
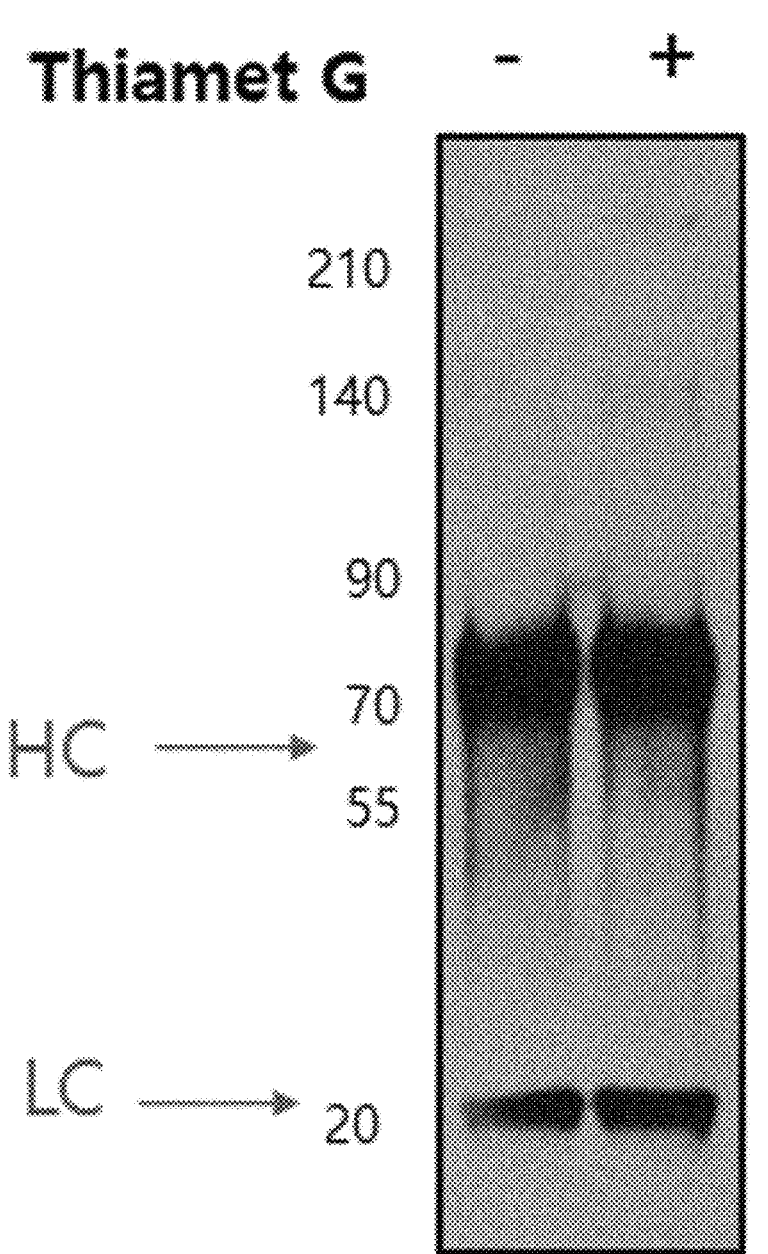
FIG. 6B illustrates results obtained by comparing, through Western blotting using a human immunoglobulin-specific antibody, the amount of the rituximab antibody that is used in the third and fourth in FIG. 6A.

To identify whether the rituximab was present at the same amount, the O-linked N-acetylglucosamine (O-GlcNAc)-specific antibody (RL2-HRP) bound to the nitrocellulose membrane was removed by stripping; incubation with anti-human-HRP and anti-mouse-HRP antibodies (rituximab is a human/mouse chimeric antibody) was performed at room temperature for 30 minutes; and then washing with TBS-T was performed three times for 10 minutes each. The ECL solution was used to sensitize an x-ray film (FIG. 6B). As a result, it was shown in FIG. 6B that although the same amount of rituximab was used, in a case of being treated with Thiamet-G, a higher amount of O-linked N-acetylglucosamine (O-GlcNAc) is bound to the rituximab as in FIG. 6A. That is, it was found that in a case of being treated with Thiamet-G, the degree of binding of O-GlcNAc in the rituximab increased, and thus the expression level thereof also increased.

Figure 7A:
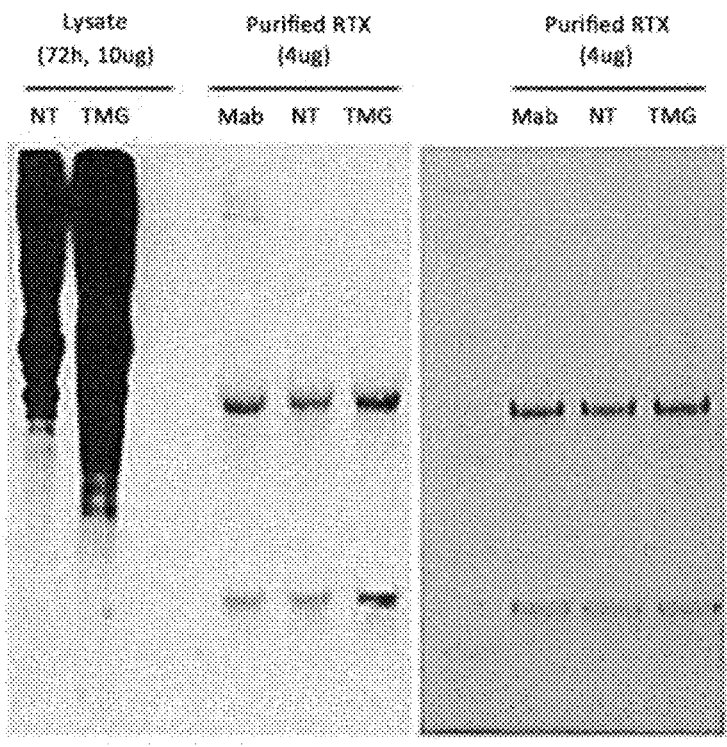
FIG. 7A illustrates results obtained by analyzing, through Western blotting using an O-linked N-acetylglucosamine-specific antibody (RL2) under reducing conditions, the degree of binding of O-linked N-acetylglucosamine (O-GlcNAc) in a host cell lysate and a rituximab antibody isolated and purified therefrom in a case where Thiamet G is added and a case where Thiamet G is not added.
Figure 7B:
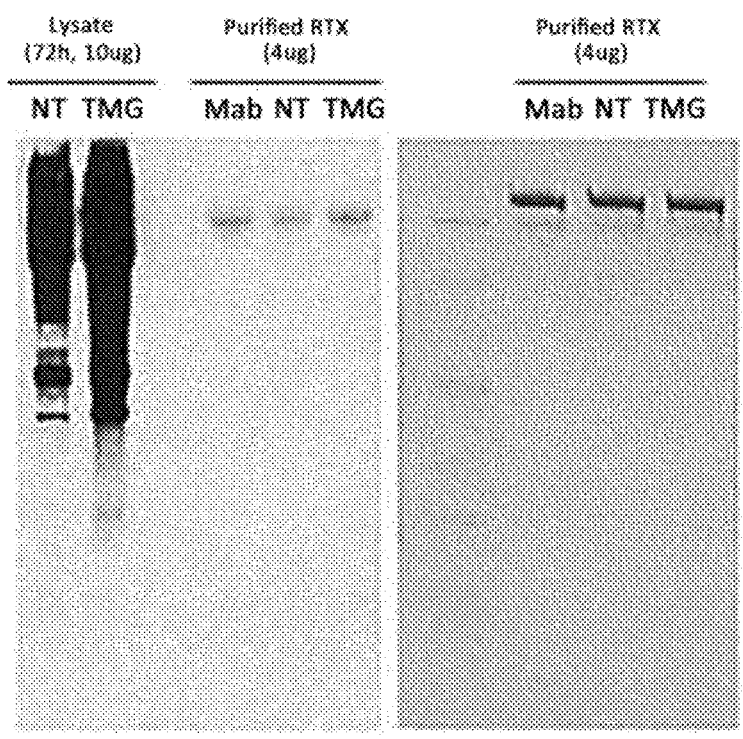
FIG. 7B illustrates results obtained by analyzing, through Western blotting using an O-linked N-acetylglucosamine-specific antibody (RL2) under non-reducing conditions, the degree of binding of O-linked N-acetylglucosamine (O-GlcNAc) in a host cell lysate and a rituximab antibody isolated and purified therefrom in a case where Thiamet G is added and a case where Thiamet G is not added.

A rituximab stable cell line was produced with a lentivirus system. The cell line was cultured for 72 hours in a serum-free RPMI medium treated with Thiamet-G (TMG) at 50

μM, and then harvested. Then, a cell lysate was prepared. In addition, the cell line was cultured in a serum-free RPMI medium, which was treated with Thiamet-G at 50 uM, in a 30° C. incubator for 2 weeks, and then the rituximab was isolated with protein A. 1 μg of the isolated antibody was subjected to immunoblotting with an anti-O-GlcNAc antibody (RL2-HRP) by performing Western blotting under reducing and non-reducing conditions; and run on an SDS gel. Then, Coomassie blue staining was performed. The results are illustrated in FIGS. 7A-7B. Here, however, as a control, Mabthera (Mab) (Roche) was used. As a result, it was found that O-GlcNAc increased in the group in which rituximab was treated with Thiamet-G.

Figure 8:
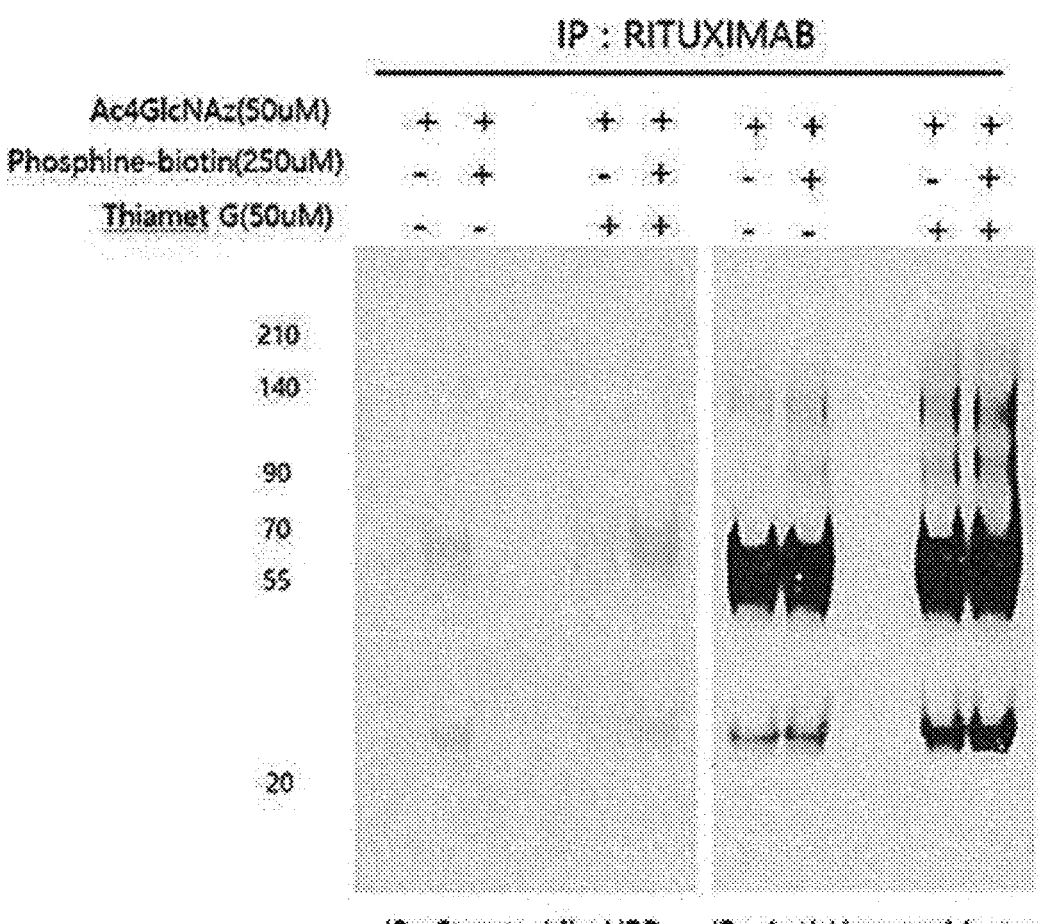
FIG. 8 illustrates results obtained by analyzing, using metabolic labeling, the degree of binding of O-linked N-acetylglucosamine (O-GlcNAc) in a host cell lysate and a rituximab antibody isolated and purified therefrom in a case where Thiamet G is added and a case where Thiamet G is not added.

To further identify differences in degree of binding of O-GlcNAc in antibody, a comparison of O-GlcNAc binding amount using metabolic labeling wax performed. A rituximab stable cell line was produced with a lentivirus system. The cell line was treated with Thiamet-G at 50 μM and Ac4GlcNAz (azido sugar) at 50 μM and cultured for 4 days. Then, rituximab was isolated with protein A. The isolated rituximab was subjected to click reaction with phosphine-biotin at room temperature for 16 hours, and then subjected to immunoblotting with streptavidin-HRP by performing Western blotting. O-GlcNAc in the rituximab was subjected to metabolic labeling. In addition, to find out the rituximab amount, for the experiment results, stripping was performed, and then immunoblotting with anti-human IgG-HRP and anti-mouse IgG-HRP was performed. As a result, it was found that as illustrated in FIG. 8, O-GlcNAc increased in the group in which the rituximab was treated with Thiamet-G.

Example 4: Identification of O-Linked Glycosylation Site in Antibody

Figure 9:
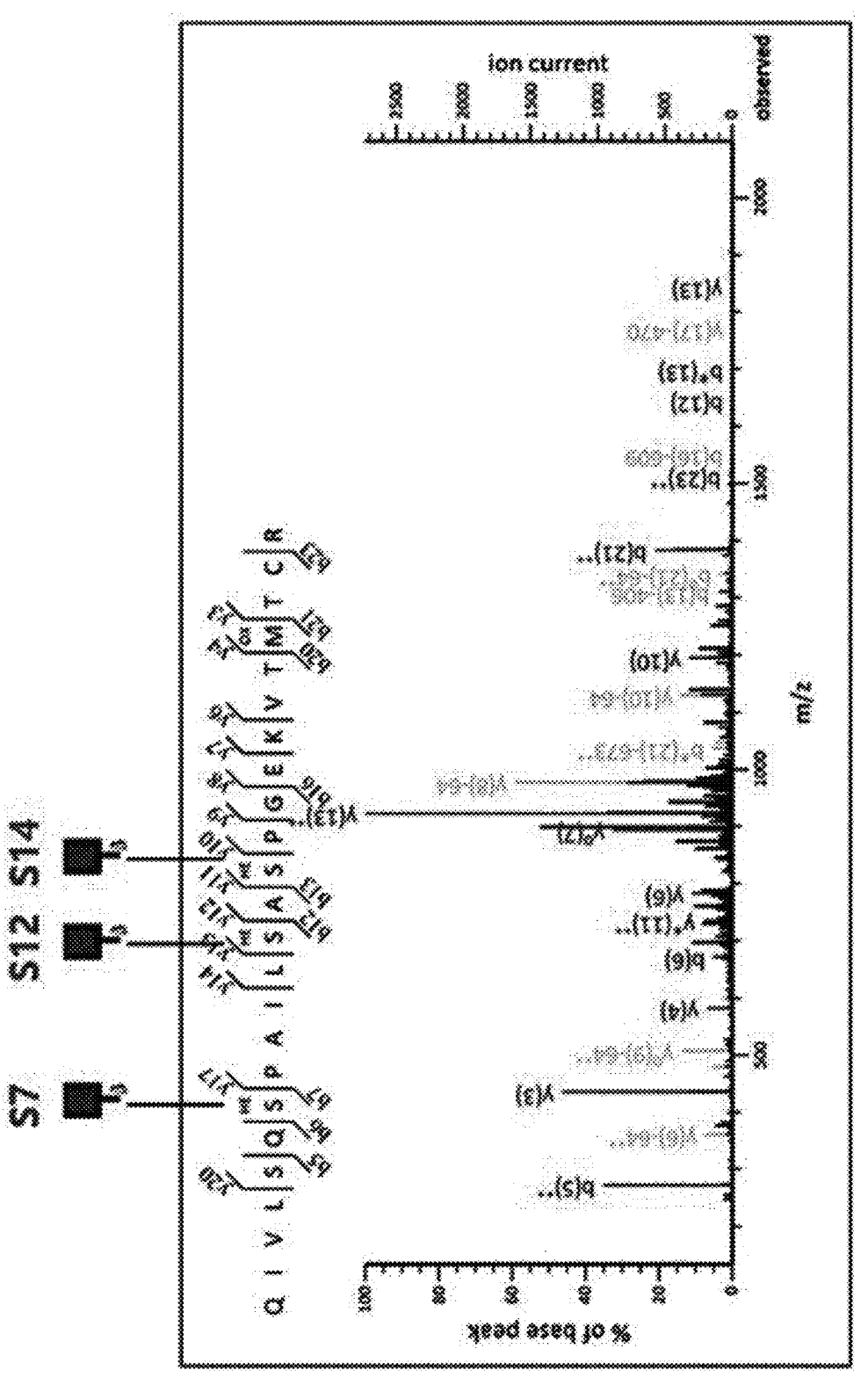
FIG. 9 illustrates positions of serine residues, to which O-GlcNAc is bound and which are obtained through LC-MS/MS analysis, in the light chain of a rituximab antibody in a case where Thiamet-G is added.
Figures 10, 11:
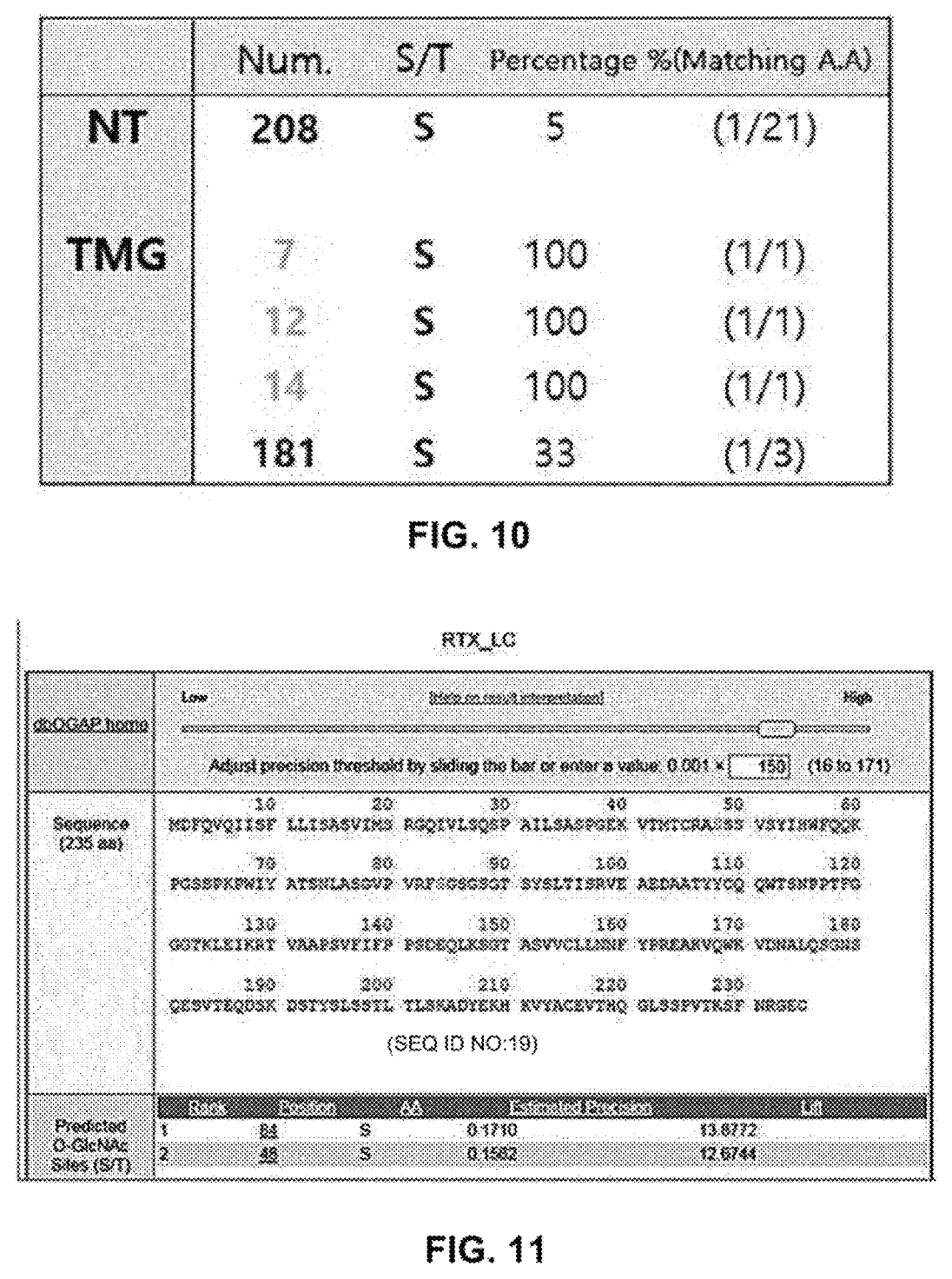

To identify an O-linked glycosylation site in a rituximab antibody, the following experiment was performed. The protein band obtained by performing the electrophoresis on an SDS-PAGE gel as described above was cut into several pieces, and then washing with 25 mM ammonium bicarbonate buffer (pH 7.8, containing 50% (v/v) acetonitrile (ACN)) was performed at room temperature for 1 hour. Then, dehydration was performed for 10 minutes in a centrifugal vacuum concentrator (Biotron, Inc., Incheon, Korea), and then rehydration was performed in 50 ng of sequencing-grade trypsin solution (Promega, Madison, WI, USA). Incubation was performed for 16 hours in 25 mM ammonium bicarbonate buffer, and then peptide isolation was performed with formic acid. Then, the peptide solution was subjected to desalting on a reversed-phase column (Gobom et al., 1999) before mass spectrometry to be performed. For LC-MS/MS analysis, analysis was performed with a nano ACQUITY UPLC and LTQ-orbitrap-mass spectrometer (Thermo Electron, San Jose, CA), and the column used was BEH C18 1.7 μm, 100 μm×100 mm column (Waters, Milford, MA, USA). The individual spectra from MS/MS were processed using the SEQUEST software (Thermo Quest, San Jose, CA, USA), and then a peak list was generated with the MASCOT program (Matrix Science Ltd., London, UK) (FIGS. 9-10). As a result, it can be seen that in a case where treatment with Thiamet-G was performed, O-linked glycosylation occurred by binding of N-acetylglucosamine to serine residues at the $7^{th}$, $12^{th}$, $14^{th}$, and $181^{st}$ positions from the 5' end of the light chain of the antibody, as compared with a case where no treatment was performed.

To predict an O-linked glycosylation site in a rituximab antibody, the following experiment was performed. For the rituximab treated with Thiamet-G, the location where N-acetylglucosamine was bound in the light chain was identified using an application-providing program (OGAP) (Wang et al., BMC Bioinformatics, 2011, 12:91), with the threshold of the program being set to 150. FIG. 11 illustrates results in a case where a signal peptide consisting of 22 amino acids was included in the light chain of the rituximab. As a result, it can be seen that O-linked glycosylation occurred by binding of N-acetylglucosamine to serine residues at the $26^{th}$ and $62^{nd}$ positions from the 5' end of the light chain of the rituximab.

Example 5: Identification of Absence of O-GlcNAc-Binding Effect

Figure 12A:
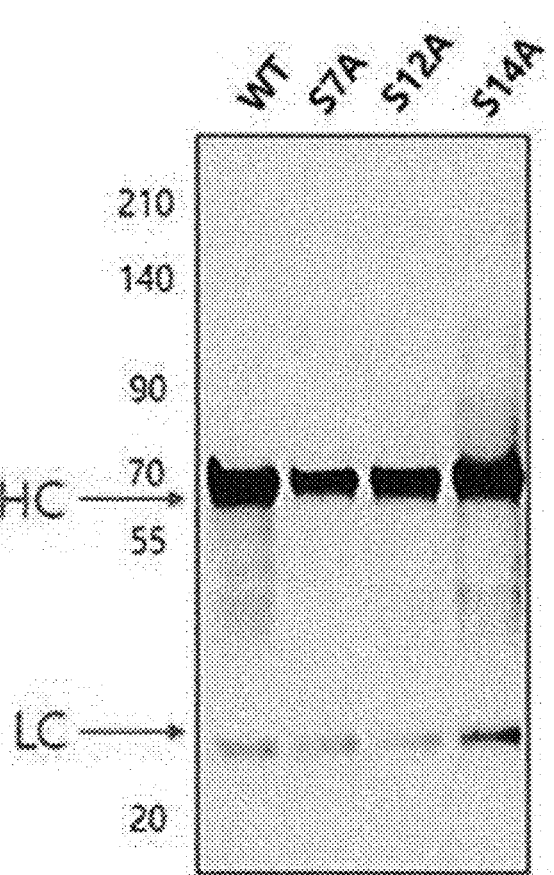
FIG. 12A illustrates results obtained by analyzing, through Western blotting, changes in expression level of the heavy and light chains of a rituximab antibody in a case where Thiamet-G is added, when the rituximab antibody, for which site-directed mutagenesis from serine residues at the $7^{th}$, $12^{th}$, and $14^{th}$ positions from the 5' end of the light chain variable region of the rituximab to alanine residues has been induced, is expressed using host cells.
Figure 12B:
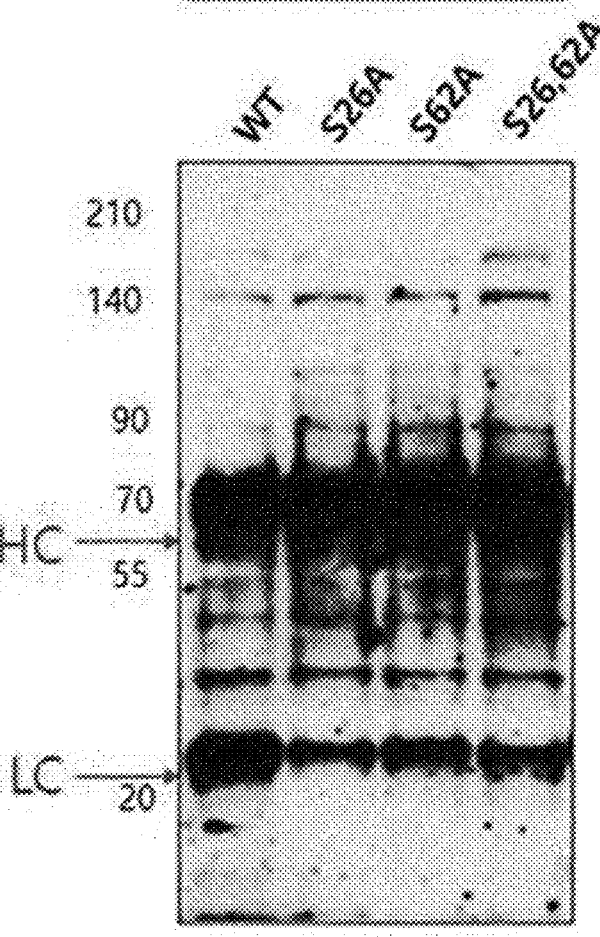
FIG. 12B illustrates results obtained by analyzing, through Western blotting, changes in expression level of the heavy and light chains of a rituximab antibody in a case where Thiamet-G is added, when the rituximab antibody, for which site-directed mutagenesis from serine residues at the $26^{th}$ and $62^{nd}$ positions from the 5' end of the light chain variable region of the rituximab to alanine residues has been induced, is expressed using host cells.

Absence of O-GlcNAc-binding effect caused by mutagenesis in O-GlcNAc binding site was further identified. In this study, an antibody was produced in the same manner as described in Example 1 above, except that for serine residues at the $7^{th}$, $12^{th}$, and $14^{th}$ positions, to which O-linked N-acetylglucosamine (O-GlcNAc) was identified to bind during mass spectrometry as illustrated in Example 4 above, and serine residues at the $26^{th}$ and $62^{nd}$ positions, to which O-GlcNAc was predicted to bind, site-directed mutagenesis from such serine residues to alanine residues was induced, and then the antibody production was analyzed. Specifically, HEK293T cells were transformed with wild-type and mutant rituximab heavy and light chains at 1:1, and then cultured, in which the other conditions were the same as described in Example 1 above. When 24 hours elapsed, the cell culture medium was removed and washing with PBS was performed three times. To this was added a lysis buffer (150 mM NaCl, 5 mM NaEDTA, 10% glycerol, 20 mM Tris-HCl (pH 8.0), 0.5% Triton X-100, and proteinase inhibitors (Complete, Roche Applied Science)). The cells were collected and transferred to a clean tube. Then, cell lysis was performed using sonication, and then centrifugation was performed at 13200 rpm for 10 minutes at 4° C. Only the supernatant was transferred separately to a clean tube, and then a cell lysate was obtained. The total protein was quantified by the Bradford method. Based on the total protein amount, electrophoresis was performed on acrylamide gel so that proteins were separated by size, and then the proteins were transferred to a nitrocellulose membrane. Portions other than the proteins electrically transferred to the nitrocellulose membrane were blocked with TBS-T containing 5% non-fat milk and 0.1% Tween 20 at room temperature for 1 hour. Incubation with anti-human-HRP and anti-mouse-HRP antibodies was performed at room temperature for 30 minutes, and then washing with TBS-T was performed three times for 10 minutes each. The ECL solution was used to sensitize an x-ray film (FIG. 12). As a result, it was found that for the rituximab antibody, in a case where the serine residues at the $7^{th}$, $12^{th}$, $26^{th}$, and $62^{nd}$ positions from the 5' end of the light chain variable region were substituted with alanine residues, the production of the heavy and light chains of the antibody decreased remarkably.

Figure 13:
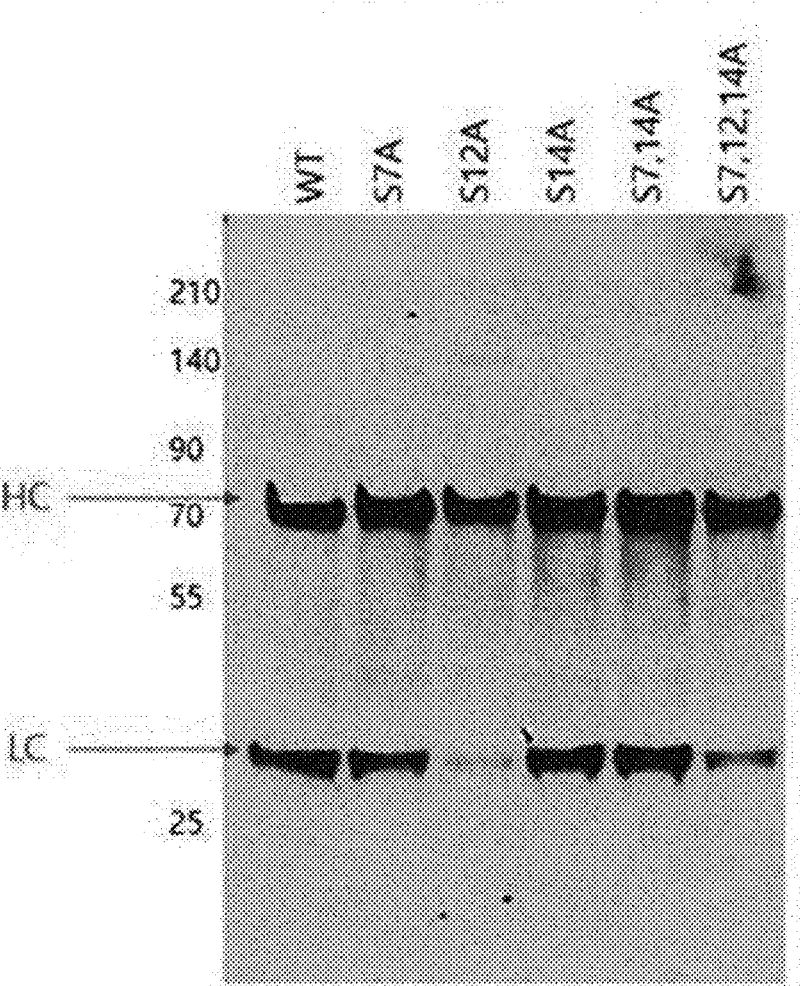
FIG. 13 illustrates results obtained by analyzing, through Western blotting, changes in expression level of the heavy and light chains of a rituximab antibody in a case where Thiamet-G is added, when the rituximab antibody, for which site-directed mutagenesis from serine residues at the $7^{th}$, $12^{th}$, and $14^{th}$ positions from the 5' end of the light chain variable region of the rituximab to alanine residues has been induced, is expressed using host cells.

Site-directed mutagenesis was induced in a rituximab antibody in the same manner as described above, except that as host cells, CHO-K1 cells were used in place of HEK293T cells. When 24 hours elapsed after transformation, the cell culture medium was removed and a serum-free RPMI medium was added. Culture was additionally performed at 30° C. for 5 days, and the medium was harvested. The same volume of medium was subjected to electrophoresis so that proteins were separated by size, and then the proteins were transferred to a PVDF membrane. Portions other than the proteins electrically transferred to the membrane were blocked with TBS-T containing 5% non-fat milk and 0.1% Tween 20 at room temperature for 1 hour. Incubation with anti-human-HRP and anti-mouse-HRP antibodies was performed at room temperature for 30 minutes, and then washing with TBS-T was performed three times for 10 minutes each. The ECL solution was used to sensitize an x-ray film (FIG. 13). As a result, it was found that for the rituximab antibody, in a case where the serine residue, in particular, one at the $12^{th}$ position from the 5' end of the light chain variable region was substituted with an alanine residue, the production of the heavy and light chains of the antibody decreased remarkably.

Example 6: Identification of Maintenance of Antibody Titer

Figure 14:
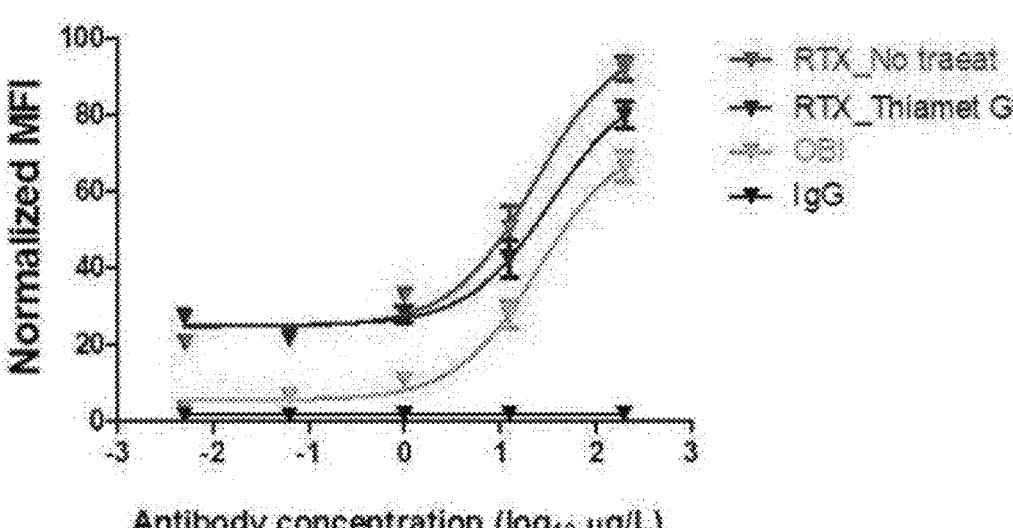
FIG. 14 graphically illustrates results obtained by analyzing the binding affinity of a rituximab antibody to its antigen in a case where Thiamet G is added and a case where Thiamet G is not added.

Identification of Binding Affinity: to identify whether O-linked glycosylation in the light chain of the rituximab caused changes in antibody titer, Ramos cells were suspended, at $1 \times 10^5$ cells per tube, in 50 µl of PBS, and were treated with the rituximab, which was produced under each condition, and obinutuzumab (OBI), which is known to bind to the same target as rituximab, at an amount of 0.1, 0.3, 1, 3, or 10 µg/ml. Then, incubation was performed at 4° C. for 30 minutes. Washing with PBS was performed once, and then treatment with anti-human Ig Fc-specific FITC-conjugated secondary antibody (109-095-008, 1:200 dilution; Jackson Laboratories), which was diluted 1:500 with 50 µl PBS, was performed. Incubation was performed at 4° C. for 30 minutes. Washing with PBS was performed once, and then flow cytometry (FACS, BD Biosciences, Franklin Lakes, NJ, USA) was used to count a total of 10,000 cells. Analysis was performed with the FlowJo software (FIG. 14). As a result, it was found that the rituximab, which underwent O-linked glycosylation by treatment with Thiamet-G, exhibited no difference in binding affinity to the rituximab obtained without any treatment.

Figure 15:
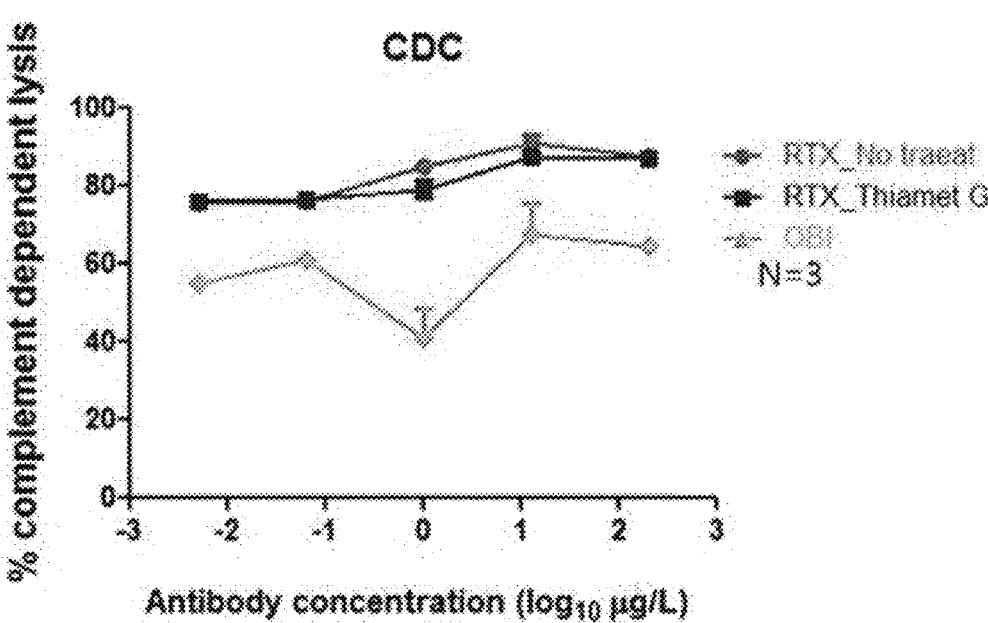
FIG. 15 graphically illustrates results obtained by analyzing the complement-dependent cytotoxicity of a rituximab antibody in a case where Thiamet G is added and a case where Thiamet G is not added.

Complement-Dependent Cytotoxicity (complementary dependent cell death): Ramos cells were treated with 5 uM of calcein-AM in a serum-free RPMI, and then incubated at 37° C. for 30 minutes. The stained Ramos cells were dispensed in an amount of $1 \times 10^5$ cells/well. Then, treatment with the rituximab, which was produced under each condition, obinutuzumab, or human IgG at an amount of 0.1, 0.3, 1, 3, or 10 ug/ml was performed, and incubation was performed at 37° C. for 10 minutes. To this was added rabbit complement MA (Cedarlane, Cat #CL3221) at a ratio of 1:4, and incubation was performed in a CO$_2$ incubator at 37° C. for 2 hours. Subsequently, for the cells, the FACSVerse (BD Biosciences) machine was used to count a total of 10,000 cells, and analysis was performed with the FlowJo software (FIG. 15). As a result, it was found that the rituximab, which underwent O-linked glycosylation by treatment with Thiamet-G, exhibited no difference in complement-dependent cytotoxicity to the rituximab obtained without any treatment.

Figure 16:
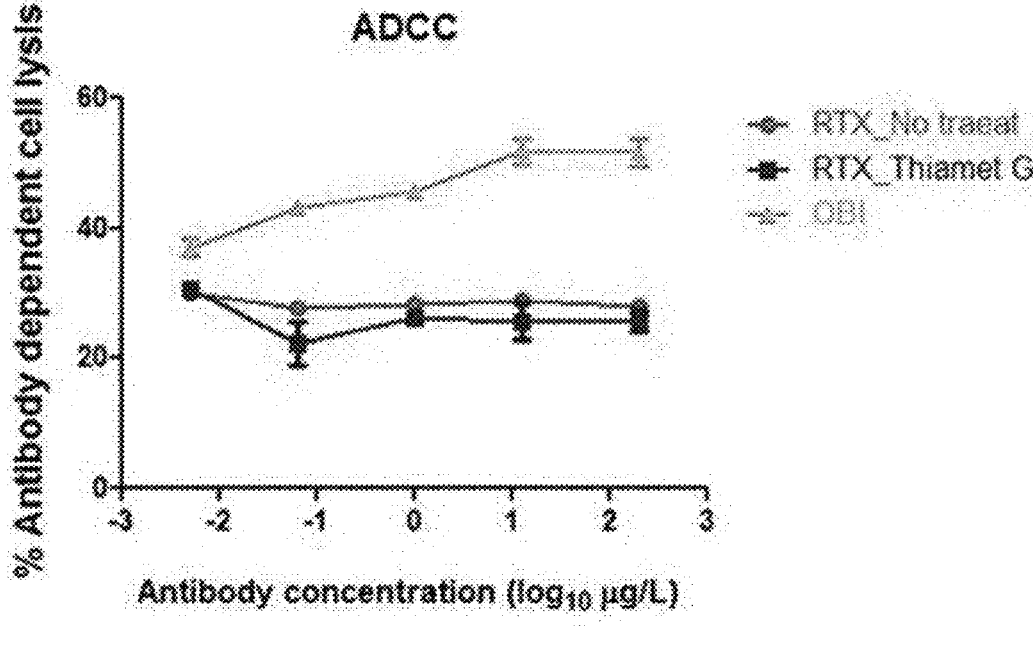
FIG. 16 graphically illustrates results obtained by analyzing the antibody-dependent cell-mediated cytotoxicity of a rituximab antibody in a case where Thiamet G is added and a case where Thiamet G is not added.

Antibody-Dependent Cell-Mediated Cytotoxicity: Ramos cells were treated with calcein-AM at 37° C. for 30 minutes in a CO$_2$ incubator, and then the cells were centrifuged. The Ramos cells were inoculated at $1 \times 10^5$ cells per tube, and then treated with the rituximab, which was produced under each condition, obinutuzumab (OBI), or human IgG at an amount of 0.1, 0.3, 1, 3, or 10 µg/ml. Then, incubation was performed at 37° C. for 10 minutes. All supernatant was removed, and resuspension was performed with 100 µl of medium. To this were added peripheral blood mononuclear cells (PBMCs) isolated from human blood at a ratio of 1:25, and incubation was performed in a CO$_2$ incubator at 37° C. for 4 hours. Subsequently, for the cells, the FACSVerse (BD Biosciences) machine was used to count a total of 10,000 cells, and analysis was performed with the FlowJo software (FIG. 16). As a result, it was found that the rituximab, which underwent O-linked glycosylation by treatment with Thiamet-G, exhibited no difference in antibody-dependent hemolysis to the rituximab obtained without any treatment.

Example 7: Sugar-Equalizing Effect Caused by Thiamet-G

Figure 17A:
FIG. 17A illustrates results obtained by analyzing, through Western blotting using a lectin (Jacalin-HRP) that binds to O-GalNAc, differences in degree of binding of O-GalNAc in rituximab antibody in a case where Thiamet G is added and a case where Thiamet G is not added.
Figure 17A:
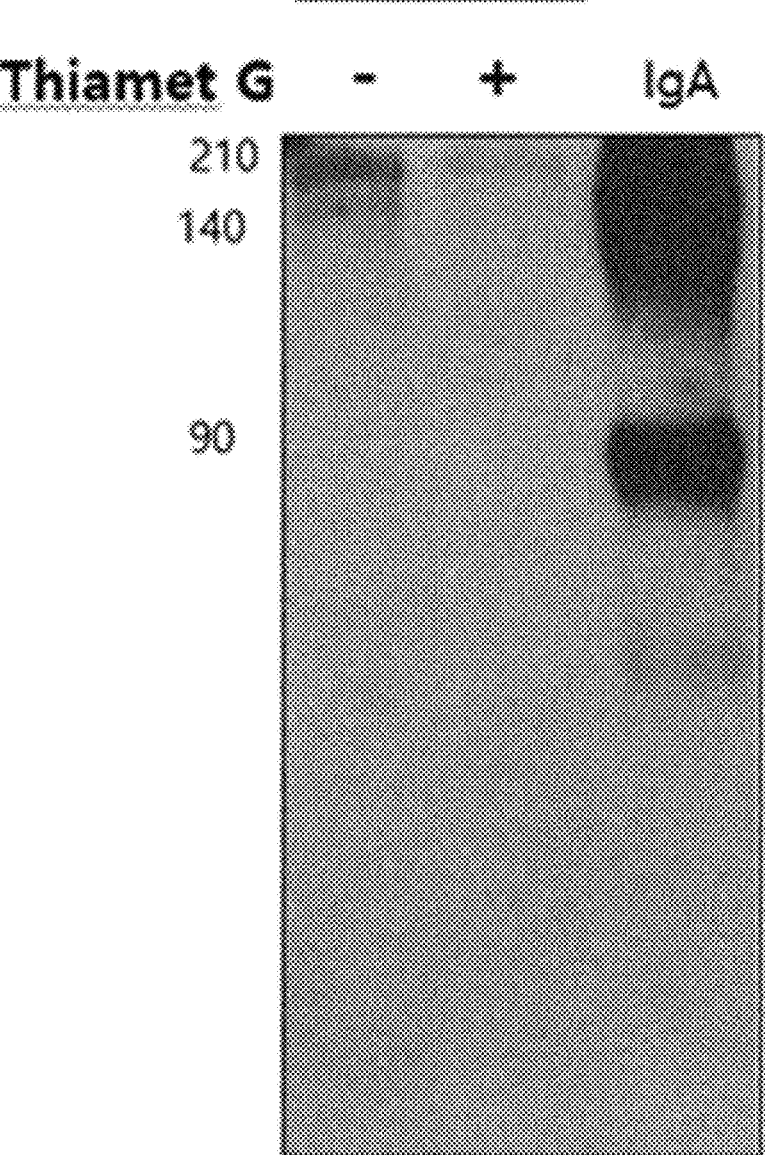
Figure 17B:
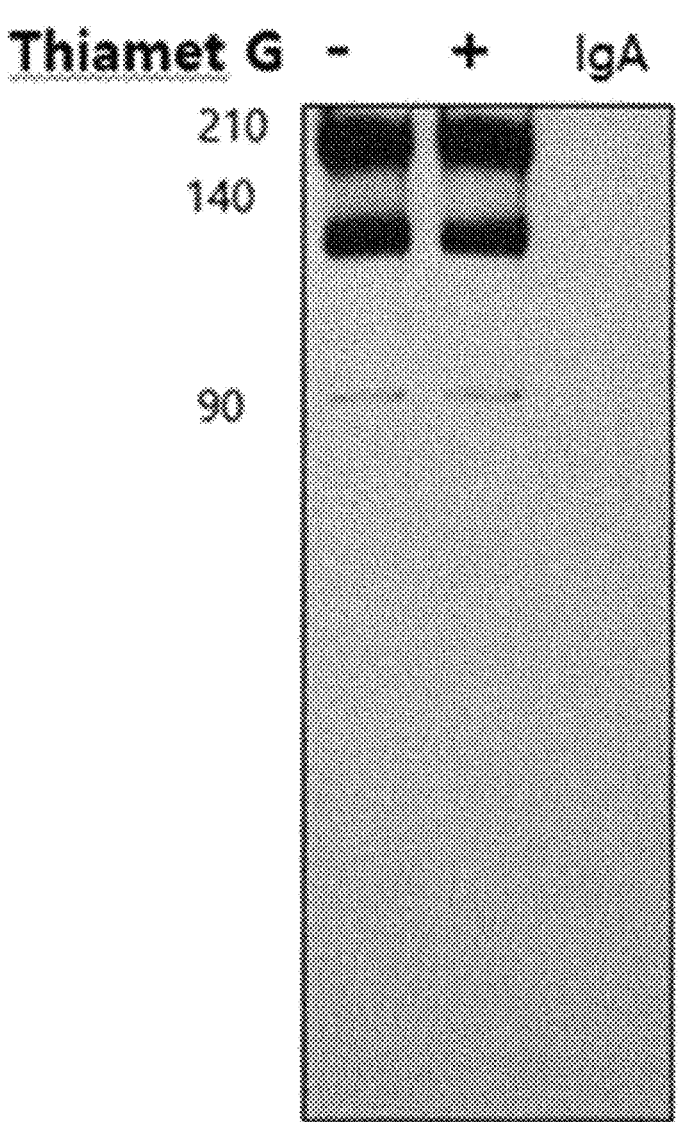
FIG. 17B illustrates results obtained by comparing, through Western blotting using a human immunoglobulin-specific antibody, the amount of the rituximab antibody that is used in the first and second in FIG. 17A.

Based on its total protein amount, the rituximab obtained in Example 1 above was added to a non-reducing sample buffer and subjected to electrophoresis on acrylamide gel, and then transferred to a nitrocellulose membrane. The nitrocellulose membrane was blocked with PBS-T (Tween 0.5%) for 1 hour. Then, an O-GalNAc-binding lectin (biotinylated-Jacalin) was added thereto, and incubation was performed at room temperature for 1 hour. Washing with PBS-T was performed three times for 10 minutes each, and then incubation with streptavidin-HRP was performed at room temperature for 30 minutes. Washing with PBS-T was performed three times for 10 minutes each, and then the ECL solution was used to sensitize an x-ray film. To identify whether the rituximab was present at the same amount, stripping was performed, and then incubation with anti-human-HRP and anti-mouse-HRP antibodies was performed at room temperature for 30 minutes. Then, washing with TBS-T was performed three times for 10 minutes each. The ECL solution was used to sensitize an x-ray film (FIGS. 17A-17B). As a result, it was shown that based on the results in FIG. 17B, for the rituximab not treated with Thiamet-G, even though the rituximab antibody at the same amount was used, a lesser amount of O-linked N-acetylgalactosamine (O-GalNAc) was bound thereto as in FIG. 17A. That is, it was found that for the rituximab obtained by treatment with Thiamet-G, O-GalNAc, which is in a bulky extension, decreased. In addition, LC-MS/MS analysis was performed in the same manner as described above to identify a residue to which O-GalNAc was bound in the rituximab obtained by treatment with Thiamet-G (FIG. 18). As a result, it was found that for the rituximab obtained without any treatment, O-GalNAc was bound to 7 residues contained in the light chain. However, it was found that in a case where treatment with Thiamet-G was performed, binding of O-GalNAc decreased in 5 out of the 7 residues.

Example 8: Identification of Increased Antibody Production

Each of the cell lines, which express rituximab, nivolumab, and pembrolizumab, respectively, was cultured at $1 \times 10^6$ cells on a 60 mm plate. The next day, treatment with Thiamet-G at 50 µM in 3 ml of CHO medium was performed, and culture was performed at 30° C. for 2 weeks. Then, the medium was harvested. The same volume of medium was subjected to electrophoresis so that proteins were separated by size, and then the proteins were transferred to a PVDF membrane. Portions other than the proteins electrically transferred to the membrane were blocked with TBS-T containing 5% non-fat milk and 0.1% Tween 20 at room temperature for 1 hour. Incubation with anti-human-HRP and anti-mouse-HRP antibodies (rituximab is a human/mouse chimeric antibody) was performed at room temperature for 30 minutes, and then washing with TBS-T was performed three times for 10 minutes each. The ECL solution was used to sensitize an x-ray film (FIG. 19), and changes in production depending on treatment with Thiamet-G were measured for each antibody (FIG. 20). As a result, it was found that upon expression of all of the rituximab, nivolumab, and pembrolizumab antibodies, in a case where treatment with Thiamet-G was performed, the production of the light chain increased remarkably by two or more times. The resulting light chain sequences of rituximab, nivolumab, and pembrolizumab, the production of which increased by treatment of Thiamet-G, were compared using CLUSTAWL (FIG. 21). As a result, it was found that all three antibodies contained serine residues at the $7^{th}$, $12^{th}$, and $14^{th}$ positions from the 5' end.

Figure 22:
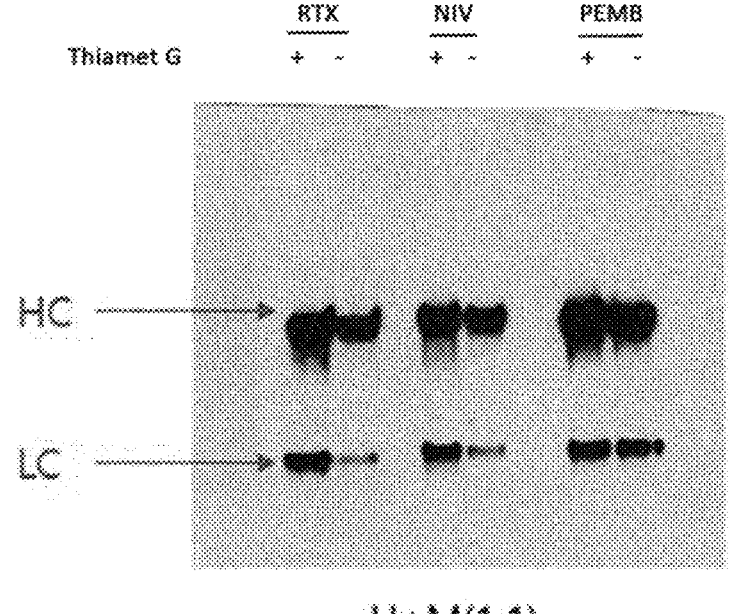
FIG. 22 illustrates results obtained by analyzing, through Western blotting, changes in expression level of the heavy and light chains of each antibody after addition of Thiamet-G (Tg), when each of rituximab (RTX), nivolumab (NIV), and pembrolizumab (PEMB) is expressed using host cells.
Figure 23:
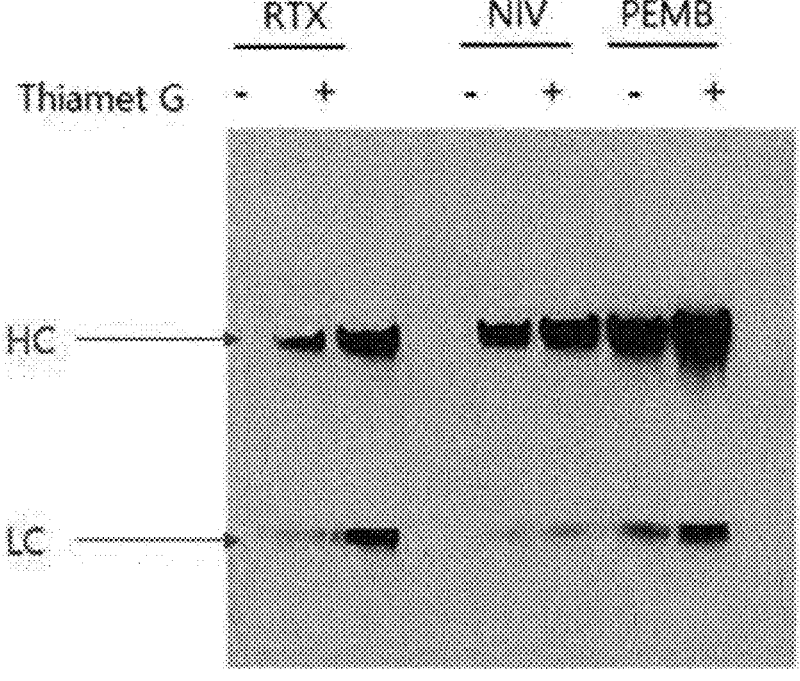
FIG. 23 illustrates results obtained by analyzing, through Western blotting, changes in expression level of the heavy and light chains of each antibody after addition of Thiamet-G (Tg), when each of rituximab (RTX), nivolumab (NIV), and pembrolizumab (PEMB) is expressed using host cells.

Next, each of the CHO cell lines, which express rituximab, nivolumab, and pembrolizumab, respectively, was cultured at $1\times10^6$ cells on a 60 mm plate. The next day, treatment with Thiamet-G at 50 µM in 3 ml of CHO medium was performed, and culture was performed at 30° C. for 7 days. Then, the medium was harvested. The same volume of medium was subjected to electrophoresis so that proteins were separated by size, and then the proteins were transferred to a PVDF membrane. Portions other than the proteins electrically transferred to the membrane were blocked with TBS-T containing 5% non-fat milk and 0.1% Tween 20 at room temperature for 1 hour. Incubation with anti-human-HRP and anti-mouse-HRP antibodies (rituximab is a human/mouse chimeric antibody) at a ratio of 1:1 or 1:2 was performed at room temperature for 30 minutes, and then washing with TBS-T was performed three times for 10 minutes each. The ECL solution was used to sensitize an x-ray film (FIGS. 22-23). As a result, it was found that upon expression of all of the rituximab, nivolumab, and pembrolizumab antibodies, in a case where treatment with Thiamet-G was performed, the production increased remarkably.

Example 9: Effect of Thiamet-G Concentration on Antibody Production

Figure 24:
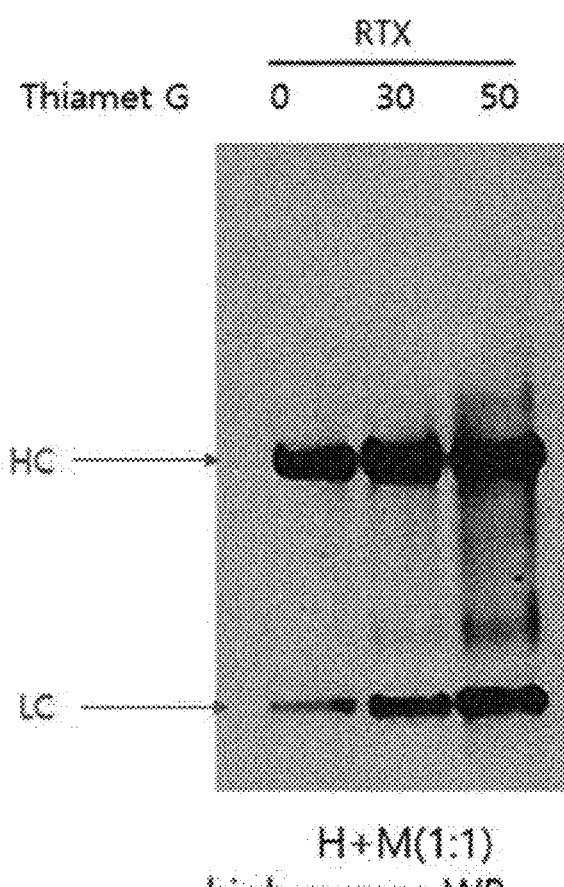
FIG. 24 illustrates results obtained by analyzing, through Western blotting (high exposure), changes in expression level of the heavy and light chains of rituximab depending on the Thiamet-G concentration added.
Figure 25:
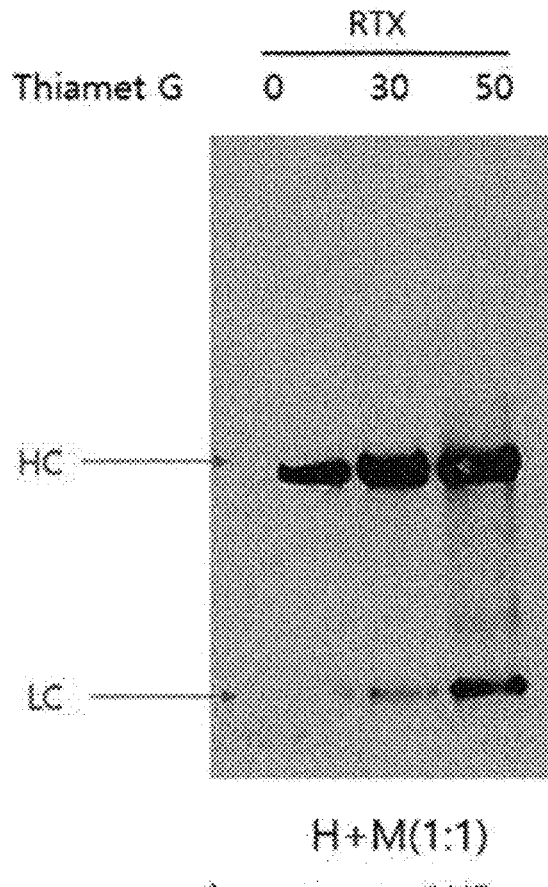
FIG. 25 illustrates results obtained by analyzing, through Western blotting (low exposure), changes in expression level of the heavy and light chains of rituximab depending on the Thiamet-G concentration added.

A rituximab antibody was produced in the same manner as in Example 1 above, except that treatment with Thiamet-G at 0, 30 or 50 µM was performed for 72 hours. The same volume of medium was subjected to electrophoresis so that proteins were separated by size, and then the proteins were transferred to a PVDF membrane. Portions other than the proteins electrically transferred to the membrane were blocked with TBS-T containing 5% non-fat milk and 0.1% Tween 20 at room temperature for 1 hour. Incubation with anti-human-HRP and anti-mouse-HRP antibodies (rituximab is a human/mouse chimeric antibody) at a ratio of 1:1 or 1:2 was performed at room temperature for 30 minutes, and then washing with TBS-T was performed three times for 10 minutes each. The ECL solution was used to sensitize an x-ray film (FIGS. 24-25). As a result, it was found that as the Thiamet-G treatment concentration increased, the production of the rituximab also increased proportionally.

In conclusion, the antibodies disclosed above and herein, in particular, the anti-CD20 antibody or anti-PD-1 antibody, obtained by causing a specific hydroxyamino acid residue in the antibody to undergo O-linked glycosylation, exhibit remarkably increased productivity while maintaining their titers at a level that is equivalent to or higher than the original antibody.

Although the present invention and its advantages have been described in detail, it should be understood that various changes, substitutions and alterations can be made herein without departing from the spirit and scope of the invention as defined in the appended claims.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. An antibody comprising at least one glycosylated hydroxyamino acid residue in the light chain thereof comprising at least one glycosylated hydroxyamino acid residue at the $7^{th}$, $12^{th}$, $14^{th}$, $26^{th}$ or $62^{nd}$ position from the 5' end of the light chain.

2. The antibody of claim 1, wherein the antibody is an anti-CD20 antibody or an anti-PD-1 antibody.

3. The antibody of claim 2, wherein the anti-CD20 antibody is a rituximab antibody that comprises at least one glycosylated hydroxyamino acid residue at the $7^{th}$, $12^{th}$, $14^{th}$, $26^{th}$, or $62^{nd}$ position from the 5' end of the light chain.

4. The antibody of claim 2, wherein the anti-PD-1 antibody is a nivolumab, pembrolizumab, or pidilizumab antibody that comprises at least one glycosylated hydroxyamino acid residue at the $7^{th}$, $12^{th}$, or $14^{th}$ position from the 5' end of the light chain.

* * * * *

SEQUENCE LISTING

<160> NUMBER OF SEQ ID NOS: 22

<210> SEQ ID NO 1
<211> LENGTH: 330
<212> TYPE: PRT
<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Ala Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
        130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
                180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
        210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
                260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330

<210> SEQ ID NO 2
<211> LENGTH: 118
<212> TYPE: PRT
<213> ORGANISM: Homo sapiens

<400> SEQUENCE: 2

Thr Phe Gly Gly Gly Thr Lys Leu Glu Ile Lys Arg Thr Val Ala Ala
1               5               10              15

Pro Ser Val Phe Ile Phe Pro Pro Ser Asp Glu Gln Leu Lys Ser Gly
                20              25              30

Thr Ala Ser Val Val Cys Leu Leu Asn Asn Phe Tyr Pro Arg Glu Ala
            35              40              45

Lys Val Gln Trp Lys Val Asp Asn Ala Leu Gln Ser Gly Asn Ser Gln
        50              55              60

Glu Ser Val Thr Glu Gln Asp Ser Lys Asp Ser Thr Tyr Ser Leu Ser
65              70              75              80

Ser Thr Leu Thr Leu Ser Lys Ala Asp Tyr Glu Lys His Lys Val Tyr
                85              90              95

Ala Cys Glu Val Thr His Gln Gly Leu Ser Ser Pro Val Thr Lys Ser
```

-continued

```
                      100                105                110

Phe Asn Arg Gly Glu Cys
        115

<210> SEQ ID NO 3
<211> LENGTH: 121
<212> TYPE: PRT
<213> ORGANISM: Mus musculus

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 4
<211> LENGTH: 95
<212> TYPE: PRT
<213> ORGANISM: Mus musculus

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro
                85                  90                  95

<210> SEQ ID NO 5
<211> LENGTH: 451
<212> TYPE: PRT
<213> ORGANISM: Artificial Sequence
<220> FEATURE:
<223> OTHER INFORMATION: Heavy chain

<400> SEQUENCE: 5

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

-continued

```
Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
```

450

<210> SEQ ID NO 6
<211> LENGTH: 213
<212> TYPE: PRT
<213> ORGANISM: Artificial Sequence
<220> FEATURE:
<223> OTHER INFORMATION: Light chain

<400> SEQUENCE: 6

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 7
<211> LENGTH: 113
<212> TYPE: PRT
<213> ORGANISM: Artificial Sequence
<220> FEATURE:
<223> OTHER INFORMATION: Nivolimab heavy chain variable region

<400> SEQUENCE: 7

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80
```

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 8
<211> LENGTH: 107
<212> TYPE: PRT
<213> ORGANISM: Artificial Sequence
<220> FEATURE:
<223> OTHER INFORMATION: Nivolimab light chain variable region

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 9
<211> LENGTH: 440
<212> TYPE: PRT
<213> ORGANISM: Artificial Sequence
<220> FEATURE:
<223> OTHER INFORMATION: Nivolumab heavy chain

<400> SEQUENCE: 9

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

-continued

```
Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
        180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```

```
<210> SEQ ID NO 10
<211> LENGTH: 214
<212> TYPE: PRT
<213> ORGANISM: Artificial Sequence
<220> FEATURE:
<223> OTHER INFORMATION: Nivolumab light chain

<400> SEQUENCE: 10
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Ser Ser Asn Trp Pro Arg
                85              90                  95

Thr Phe Gly Gln Gly Thr Lys Val Glu Ile Lys Arg Thr Val Ala Ala
            100             105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150                 155                 160

Glu Ser Val Thr Glu Gln Asp Ser Lys Asp Ser Thr Tyr Ser Leu Ser
                165             170                 175

Ser Thr Leu Thr Leu Ser Lys Ala Asp Tyr Glu Lys His Lys Val Tyr
            180             185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 11
<211> LENGTH: 120
<212> TYPE: PRT
<213> ORGANISM: Artificial Sequence
<220> FEATURE:
<223> OTHER INFORMATION: Pembrolizumab heavy chain variable region

<400> SEQUENCE: 11

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20              25                  30

Tyr Met Tyr Trp Val Arg Gln Ala Pro Gly Gln Gly Leu Glu Trp Met
        35              40                  45

Gly Gly Ile Asn Pro Ser Asn Gly Gly Thr Asn Phe Asn Glu Lys Phe
    50              55                  60

Lys Asn Arg Val Thr Leu Thr Thr Asp Ser Ser Thr Thr Thr Ala Tyr
65              70                  75                  80

Met Glu Leu Lys Ser Leu Gln Phe Asp Asp Thr Ala Val Tyr Tyr Cys
                85              90                  95

Ala Arg Arg Asp Tyr Arg Phe Asp Met Gly Phe Asp Tyr Trp Gly Gln
            100             105                 110

Gly Thr Thr Val Thr Val Ser Ser
            115                 120

<210> SEQ ID NO 12
<211> LENGTH: 119
<212> TYPE: PRT
<213> ORGANISM: Artificial Sequence
<220> FEATURE:
<223> OTHER INFORMATION: Pembrolizumab light chain variable region

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20              25                  30

Gly Tyr Ser Tyr Leu His Trp Tyr Gln Gln Lys Pro Gly Gln Ala Pro
        35              40                  45
```

-continued

```
Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Thr
            100                 105                 110

Ser Glu Asn Leu Tyr Phe Gln
        115

<210> SEQ ID NO 13
<211> LENGTH: 447
<212> TYPE: PRT
<213> ORGANISM: Artificial Sequence
<220> FEATURE:
<223> OTHER INFORMATION: Pembrolizumab heavy chain

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

-continued

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445
```

```
<210> SEQ ID NO 14
<211> LENGTH: 218
<212> TYPE: PRT
<213> ORGANISM: Artificial Sequence
<220> FEATURE:
<223> OTHER INFORMATION: Pembrolizumab light chain

<400> SEQUENCE: 14

Glu Ile Val Leu Thr Gln Ser Pro Ala Thr Leu Ser Leu Ser Pro Gly
1                   5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
                35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205
```

```
Val Thr Lys Ser Phe Asn Arg Gly Glu Cys
    210                 215

<210> SEQ ID NO 15
<211> LENGTH: 117
<212> TYPE: PRT
<213> ORGANISM: Artificial Sequence
<220> FEATURE:
<223> OTHER INFORMATION: Pidilizumab heavy chain variable region

<400> SEQUENCE: 15

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115

<210> SEQ ID NO 16
<211> LENGTH: 106
<212> TYPE: PRT
<213> ORGANISM: Artificial Sequence
<220> FEATURE:
<223> OTHER INFORMATION: Pidilizumab light chain variable region

<400> SEQUENCE: 16

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 17
<211> LENGTH: 444
<212> TYPE: PRT
<213> ORGANISM: Artificial Sequence
<220> FEATURE:
<223> OTHER INFORMATION: Pidilizumab heavy chain

<400> SEQUENCE: 17
```

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20              25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Trp Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Trp Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Trp Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
```

-continued

```
                420             425             430
Tyr Thr Gln Lys Ser Leu Ser Leu Ser Pro Gly Lys
        435             440
```

```
<210> SEQ ID NO 18
<211> LENGTH: 212
<212> TYPE: PRT
<213> ORGANISM: Artificial Sequence
<220> FEATURE:
<223> OTHER INFORMATION: Pidilizumab light chain

<400> SEQUENCE: 18

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Trp Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

```
<210> SEQ ID NO 19
<211> LENGTH: 235
<212> TYPE: PRT
<213> ORGANISM: Artificial Sequence
<220> FEATURE:
<223> OTHER INFORMATION: rituximab light chain including signal peptide

<400> SEQUENCE: 19

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60
```

-continued

```
Pro Lys Pro Trp Ile Tyr Ala Thr Ser Asn Leu Ala Ser Gly Val Pro
65              70                  75                  80

Val Arg Phe Ser Gly Ser Gly Ser Gly Thr Ser Tyr Ser Leu Thr Ile
            85                  90                  95

Ser Arg Val Glu Ala Glu Asp Ala Ala Thr Tyr Tyr Cys Gln Gln Trp
            100             105             110

Thr Ser Asn Pro Pro Thr Phe Gly Gly Gly Thr Lys Leu Glu Ile Lys
        115             120             125

Arg Thr Val Ala Ala Pro Ser Val Phe Ile Phe Pro Pro Ser Asp Glu
        130             135             140

Gln Leu Lys Ser Gly Thr Ala Ser Val Val Cys Leu Leu Asn Asn Phe
145             150             155             160

Tyr Pro Arg Glu Ala Lys Val Gln Trp Lys Val Asp Asn Ala Leu Gln
            165             170             175

Ser Gly Asn Ser Gln Glu Ser Val Thr Glu Gln Asp Ser Lys Asp Ser
            180             185             190

Thr Tyr Ser Leu Ser Ser Thr Leu Thr Leu Ser Lys Ala Asp Tyr Glu
        195             200             205

Lys His Lys Val Tyr Ala Cys Glu Val Thr His Gln Gly Leu Ser Ser
    210             215             220

Pro Val Thr Lys Ser Phe Asn Arg Gly Glu Cys
225             230             235
```

```
<210> SEQ ID NO 20
<211> LENGTH: 55
<212> TYPE: PRT
<213> ORGANISM: Artificial Sequence
<220> FEATURE:
<223> OTHER INFORMATION: rituximab light chain

<400> SEQUENCE: 20
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala
    50                  55
```

```
<210> SEQ ID NO 21
<211> LENGTH: 59
<212> TYPE: PRT
<213> ORGANISM: Artificial Sequence
<220> FEATURE:
<223> OTHER INFORMATION: nivolumab light chain

<400> SEQUENCE: 21
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu
    50                  55
```

```
<210> SEQ ID NO 22
```

-continued

```
<211> LENGTH: 54
<212> TYPE: PRT
<213> ORGANISM: Artificial Sequence
<220> FEATURE:
<223> OTHER INFORMATION: pembrolizumab light chain

<400> SEQUENCE: 22

Gln Ile Val Leu Ser Gln Ser Pro Ala Ile Leu Ser Ala Ser Pro Gly
1               5                   10                  15

Glu Lys Tyr Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala
    50
```